United States Patent [19]
Haber et al.

[11] Patent Number: 5,453,269
[45] Date of Patent: Sep. 26, 1995

[54] HETEROBIFUNCTIONAL ANTIBODIES HAVING DUAL SPECIFICITY FOR FIBRIN AND THROMBOLYTIC AGENTS AND METHODS OF USE

[75] Inventors: Edgar Haber, Princeton, N.J.; Christoph Bode, Heidelberg, Germany

[73] Assignee: The General Hospital Corporation, Boston, Mass.

[21] Appl. No.: 960,305

[22] Filed: Oct. 13, 1992

Related U.S. Application Data

[63] Continuation of Ser. No. 652,107, Feb. 8, 1991, abandoned, which is a continuation-in-part of Ser. No. 159,585, filed as PCT/US87/00860, Apr. 14, 1987, abandoned, which is a continuation-in-part of Ser. No. 851,554, Apr. 14, 1986, abandoned.

[30] Foreign Application Priority Data

Apr. 14, 1987 [WO] WIPO ............... PCT/US87/00860

[51] Int. Cl.$^6$ ................. A61K 39/395; C07K 15/28
[52] U.S. Cl. ................. 424/136.1; 530/387.3; 530/388.25; 530/388.26; 530/389.3; 435/70.21; 435/172.2; 435/240.27; 935/104; 935/107; 424/146.1; 424/158.1
[58] Field of Search ................. 424/85.8, 85.91; 530/387.3, 388.25, 388.26, 389.3, 380, 382, 389.3, 391.7; 514/2; 435/70.21, 172.2, 240.27; 935/104, 107

[56] References Cited

U.S. PATENT DOCUMENTS

| | | | |
|---|---|---|---|
| 4,273,873 | 6/1981 | Sugitachi et al. | 435/180 |
| 4,470,925 | 9/1984 | Auditore-Hargreaves | 530/387 |
| 4,474,893 | 10/1984 | Reading | 436/547 |
| 4,833,085 | 5/1989 | Schaumann et al. | 435/240.27 |

FOREIGN PATENT DOCUMENTS

| | | |
|---|---|---|
| 8500974 | 9/1983 | WIPO . |
| WO83/03679 | 10/1983 | WIPO . |
| WO87/06263 | 10/1987 | WIPO . |
| WO88/03559 | 5/1988 | WIPO . |
| WO89/09817 | 10/1989 | WIPO . |

OTHER PUBLICATIONS

Agnelli et al., Circulation 72(1):178–182 (1985).
Agnelli et al., Thrombosis and Haemostasis 63(2):204–207 (1990).
Agnelli et al., Blood 66(2):399–401 (1985).
Collen et al., Circulation 74(4):838–842 (1986).
Collen et al., Circulation 84(3):1216–1234 (1991).
Emeis et al., Arzneimittelforschung 42(3):358–362 (1992).
Gardell et al., Circulation 84(1):244–253 (1991).
Larsen et al., The Journal of Biological Chemistry 266(13):8156–8161 (1991).
Lijnen et al., The Journal of Biological Chemistry 263(12):5594–5598 (1988).
Lijnen et al., Thrombosis and Haemostasis 66(4):468–473 (1991).
Martin et al., Z. Kardiol. 79:Suppl 3, 167–170 (1990).
Matsuo et al., Thrombosis Research 42:187–194 (1986).
Sobel et al., Circulation 81(4):1362–1373 (1990).
Stump et al., Blood 69(2):592–596 (1987).
Branscomb et al., Thrombosis and Haemostasis 64:260–266 (1990).
Branscomb, E. E. et al., Thromb. Haemost. 64:260 (1990).
Bode, C. et al., Circulation 81:1974 (1990).
Charpie, J. R. et al., Biochemistry 29:6374 (1990).
Bode, C. et al., J. Biol. Chem. 264:944 (1989).
Runge, M. S. et al., Clin. Res. 36:501 (1988).
Runge, M. S. et al., Trans. Assoc. Am. Phys. 100:250 (1987).
Runge, M. S. et al., Biochemistry 27:1153 (1988).
Runge, M. S. et al., Proc. Natl. Acad. Sci., USA 84:7659 (1987).
Bode, C. et al., J. Mol. Cell Cardiol. 19:335 (1987).
Bode, C. et al., Science 229:765 (1985).
Sevilla, C. L. et al., Biochem. Biophys. Res. Commun. 130:91 (1985).
Duberstein, R., Genetic Engineering News 6:22 (1986).
Lanzavecchia A. et al., Eur. J. Immunol. 17:105 (1987).
Staerz, U. D. et al., Proc. Natl. Acad. Sci. USA 83:1453 (1986).
Milstein, C. et al., Nature 305:537 (1983).
Liu, M. A. et al., Proc. Natl. Acad. Sci. USA 82:8648 (1985).
Brennan, M. et al., Science 229:81 (1985).
Nisonoff, A. et al., Nature 194:355 (1962).
Kudryk, B. et al., Molec. Immunol. 21:89 (1984).
Hui, K. Y. et al., Science 222:1129 (1983).
Kato, K. et al., Chem. Abstr. 94:325, Abstract No. 61048j (1981).
Angles–Cano, E. R., Chem. Abstr. 104:307, Abstract No. 144639d (1986).
International Search Report for PCT/US87/00860.
Waldman, T. A., "Monocloral Antibodies in Diagnosis and Therapy," Science 252:1657–1662, 21 Jun. 1991.
Liu et al., "Hetemantibodys Duplexes Target Cells for Lysis by Cytotoxic T Lymphocytes", Proc. Natl. Acad. Sci. USA 82:8648–8652, Dec. 1985.
Hui et al., "Monoclonal Antibodies to a Synthetic Fibrin–Like Peptide Bind to Human Fibrin but not Fibrinogen," Science 222:1129–1131, 9 Dec. 1983.
Milstein et al., "Hybrid Hybridomas and Their Use in Immunohistochemistry," Nature 305:537–540, Oct. 1983.

*Primary Examiner*—David L. Lacey
*Assistant Examiner*—Robert D. Budens
*Attorney, Agent, or Firm*—Sterne, Kessler, Goldstein & Fox

[57] ABSTRACT

Heterobifunctional antibodies having dual specificities, one specificity directed against a thrombus, and the other specificity directed against a thrombolytic agent are disclosed. The invention also relates to methods of using these heterobifunctional antibodies to lyse a thrombus.

5 Claims, 19 Drawing Sheets

HETEROBIFUNCTIONAL ANTIBODIES HAVING DUAL SPECIFICITY FOR FIBRIN AND THROMBOLYTIC AGENTS AND METHODS OF USE

This application is a File Wrapper Continuation of 07/652,107, filed Feb. 8, 1991, now abandoned, which is a continuation-in-part application of U.S. application Ser. No. 07/159,585, filed Jan. 11, 1988, now abandoned, which disclosure is herein incorporated in its entirety which is the U.S. National Phase Application of PCT/US87/00860 filed Apr. 14, 1987, now abandoned, which is a Continuation-In-Part of 06/851,554 filed Apr. 14, 1986, now abandoned.

TECHNICAL FIELD

This invention relates to heterobifunctional antibodies having dual specificities, one specificity directed against a thrombus and the other specificity directed against a thrombolytic agent. This invention further relates to a method of using these heterobifunctional antibodies in immunodiagnostic and immunotherapeutic processes.

BACKGROUND ART

Most myocardial infarctions are caused by coronary thrombosis (DeWood et al., N. Eng. J. Med. 303:897 (1983). The coronary thrombosis that causes the myocardial infarction can be lysed by thrombolytic agents. These thrombolytic agents are plasminogen activators that activate the conversion of plasminogen to the fibrinolytic enzyme plasmin. Plasmin will then lyse the fibrin present in the thrombus. This treatment with plasminogen activators is not without side effects. Plasmin acts non-selectively and therefore, not only lyses the fibrin in the thrombus, but also attacks fibrinogen and clotting factors, often resulting in severe bleeding diathesis.

Streptokinase, urokinase and tissue-type plasminogen activator (TPA) are three known plasminogen activators for lysing thrombi. These activators are indicated for the treatment for acute cardiovascular disease such as infarct, stroke, pulmonary embolism, deep vein thrombosis, peripheral arterial occlusion, arid other venous thrombosis. Both streptokinase and urokinase, however, have severe limitations. Due to a low affinity for fibrin, both activators will activate circulating and fibrin-bound plasminogen indiscriminately. The plasmin formed in circulating blood is neutralized before it can be used in thrombolysis. Residual plasmin will degrade several clotting factor proteins, for example, fibrinogen, factor V, and factor VIII, causing hemorrhagic potential. Further, streptokinase is strongly antigenic and patients with high antibody titers respond inefficiently to treatment and cannot remain on continuous treatment.

Human tissue-type plasminogen activator can bind to fibrin and therefore favors the activation of plasminogen in close proximity to the thrombus, potentially sparing fibrinogen elsewhere in the circulation. However, at doses required for prompt lysis of coronary thrombi, the use of tissue-type plasminogen activator can also result in hemorrhage.

In order to increase the specificity of the thrombolytic agents to the thrombus, it has been shown that covalent linkage of urokinase to a fibrin-specific antibody results in marked enhancement of fibrinolytic potency and specificity Bode et al., Science 229:765–767 (1985).

One function characteristic of every antibody molecule is specific binding to an antigenic determinant. Antibodies in vivo are bivalent and monospecific, containing two identical antigen binding sites. The specific binding of antigen by an antibody molecule is determined by the antibody's structure of the variable regions ($F_{ab}$) of both heavy and light chains. Antibodies having dual specificities have been prepared by subjecting antibodies of different specificities to a selective cleavage of the disulfide bridges that link the two heavy chains together. Antibody half-molecules are then reassociated under neutral pH to produce the hybrid antibodies having dual specificities.

Nisonhoff et al., Nature (London) 194:355 (1962), describe the in vitro production of a bispecific antibody molecule from a polyclonal rabbit antibody, anti-ovalbumin, and an anti-bgg antibody. The monospecific antibodies were treated with pepsin to remove the $F_c$ portion of the antibody, leaving the two antigen-binding sites ($F_{ab}$) covalently linked by a single disulfide bond. This bond was then split under reducing conditions and the two antibody molecules reassociated under oxidizing conditions to produce a bispecific antibody.

In Brennan et al., Science 299:31 (1985), a chemical procedure is described for preparing bispecific antibody fragments from monoclonal antibodies. In this procedure, a modification of the Nisonoff technique was used in cleaving the $F_{ab}$ fragments, followed by reconstituting the half-fragments to form the bispecific antibody molecule. The $F_{ab}$ fragments were reduced in the presence of sodium arsenite to stabilize vicinal dithiols and impede intramolecular disulfide formation. The other modification involved activating the thiols of one of the half-$F_{ab}$ fragments as a thionitrobenzoate derivative. By this process, a bispecific antibody was produced from anti-avidin $F_{ab}$ and anti-luciferase $F_{ab}$ was produced.

Liu et al., Proc. Natal. Acad. Sci. USA 82:8648 (1985), disclose a chemical procedure for forming a bispecific antibody in which anti-T3 antibody was covalently linked to a second monoclonal antibody, anti-IgId specific for the idiotype of the surface immunoglobulin of a human B lymphoma. The anti-T3 and anti-IgId antibodies were first reacted with N-suc-cinimidyl-3-(2-pyridyldithio) propionate (SPDP). Thiol groups were attached to the cleaved anti-T3 antibody using 2-iminothiolane. Then the two modified half-antibodies, anti-T3 and anti-IgId, were mixed to covalently link the two antibodies. The result showed that the T8 cytotoxic T lymphocytes lysed the human B-lymphoma cells, but no lyses was observed when T4 cytotoxic T lymphocyte cells were used.

Bispecific antibodies have also been produced from hybridomas. The preparation of bispecific monoclonal antibodies by fusion of antibody-producing hybridoma cells is described in Milstein and Cuello, Nature (London) 305:537 (1983). This reference describes the fusion of two hybridomas, or the fusion of one hybridoma with spleen cells from an immunized rat, to produce hybrid hybridomas. These hybrid hybridomas secrete predefined bispecific monoclonal antibodies as well as monospecific antibodies. Anti-somatostatin/anti-pluroxidase and anti-substance P/anti-peroxidase bispecific monoclonal antibodies were prepared in this manner. The bispecific monoclonal antibodies produced by hybrid hybridomas were complete molecules, containing the $F_c$ region as well as the antigen-combining sites.

PCT application, WO83/03679, describes the production of a bispecific antibody having dual specificities obtained by fusion two hybridomas. This application describes procedures for producing and selecting hybrid hybridomas. The bispecific antibodies therein are described as having many potential uses, ranging from immunodiagnostic procedures to targeted delivery of drugs.

It would be desirable to have a bispecific antibody having dual specificity such that one specificity would be directed against a thrombus and the other specificity would be directed against a thrombolytic agent. With this bispecific antibody, a thrombus would be detected. This thrombus then could be lysed by the action of a thrombolytic agent that becomes or is attached to the anti-thrombolytic antibody. The lysis of thrombi is complicated; it was not known whether a bispecific antibody would block or inhibit the thrombolytic activity by the thrombolytic agent.

DESCRIPTION OF THE INVENTION

The present invention provides for a heterobifunctional antibody having dual specificity, with one specificity directed against a thrombus and the other specificity directed against a thrombolytic agent. The heterobifunctional antibody according to this invention can be used for immunodiagnosis and immunotherapy. Accordingly, the present invention also provides processes for immunodiagnosis and immunotherapy employing the heterobifunctional antibodies.

DETAILED DESCRIPTION OF THE INVENTION

Figure 1:
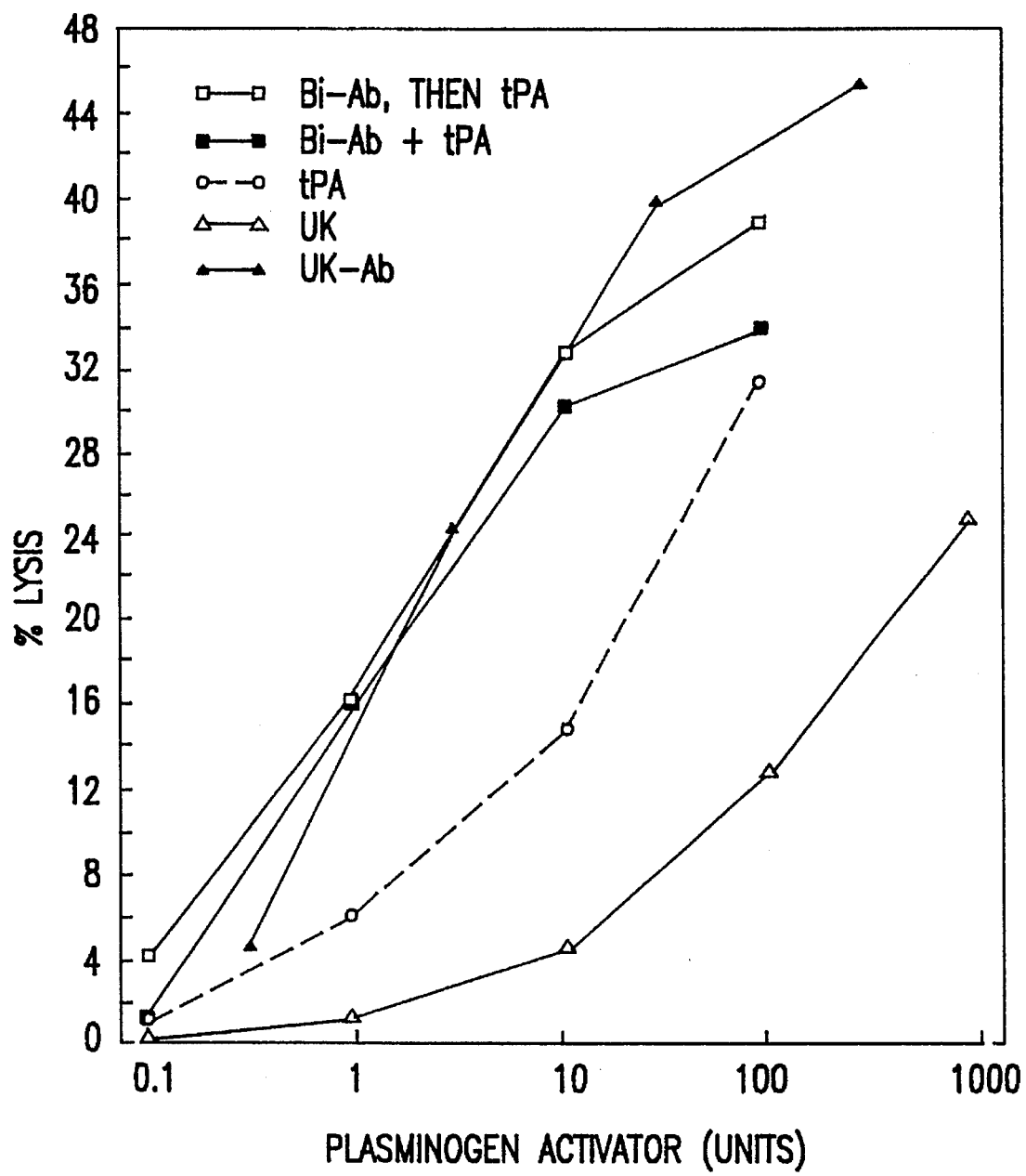
FIG. 1. The release of labeled fibrin from fibrin-Sepharose by the following compounds: (1) a heterobifunctional antibody specific for both fibrin and tissue plasminogen activator (TPA) complexed to TPA (BI-AB), then TPA); (2) a heterobifunctional antibody specific for both fibrin and TPA, first added to fibrin-Sepharose followed by the addition of TPA after washing (BI-AB+TPA); (3) a urokinase-antifibrin antibody covalent complex (UK-AB); (4) TPA alone; and (5) urokinase alone (UK). Lysis was expressed as the quotient of released radioactivity and total radioactivity. Each point represents the mean of three separate experiments with a mean standard deviation of 1.23.

This invention is directed to heterobifunctional antibodies having dual specificity with one specificity directed against a thrombus and the other specificity directed against a thrombolytic agent. The individual specificities are to (a) antigenic determinants on a thrombus and (b) antigenic determinants on a thrombolytic agent.

Throughout this specification, the term "heterobifunctional antibody" is used to designate a single antibody molecule having two specificities or two molecules linked to each other each having different specificities. Other terms have been used to describe heterobifunctional antibodies including heteroantibody, bispecific antibody, hybrid antibodies, heteroligating antibody, antibody duplex, heterodimer, among others. It will be understood by one of skill in the art that these are all equivalent terms.

The antibodies usable in preparing the heterobifunctional antibodies of the present invention may be either polyclonal or monoclonal antibodies. In the preferred embodiments of this invention, monoclonal antibodies are used in preparing heterobifunctional antibodies.

The anti-thrombus specificity as used herein refers to antibodies raised against fibrin or fibrinogen. Blood clots when thrombin cleaves two pairs of small peptides from fibrinogen to yield fibrin monomers (Blomback et al., *Ark. Kemi.* 12:173 (1958) and Doolittle, R. F., *Adv. Protein Chem.* 27:1 (1973)). Fibrin monomers spontaneously aggregate to form an insoluble gel that is covalently stabilized by Factor XIIIa. Fibrin retains 98% of the original covalent structure of fibrinogen. Thus, in the preferred embodiment of this invention the antibodies that are used to form one-half of the heterobifunctional molecule are any antibodies which are fibrin-specific and are substantially devoid of fibrinogen cross-reactivity.

For example, antibodies with this specificity have been described in Hui et al., *Science* 222:1129 (1983). Further description of the same type of antibodies can be found in commonly assigned co-pending U.S. patent application Ser. No. 824,228, filed Jan. 30, 1986, for "Fibrin-Specific Monoclonal Antibodies Lacking Fibrinogen Cross-Reactivity." Fibrinspecific monoclonal antibodies with substantially no fibrinogen cross-reactivity are also described in commonly assigned co-pending U.S. patent application Ser. No. 851,514, filed concurrently herewith. Other examples of antibodies with a specificity against a thrombus include Kudryk et al., *Mol. Imm.* 21:89 (1984). All of the above references are herein incorporated by reference.

Antibodies specific against thrombolytic agents may also be polyclonal or monoclonal antibodies, preferably monoclonal antibodies. When plasminogen is converted by an activator to plasmin, the active fibrinolytic enzyme of plasma, it develops a marked affinity for its substrate, fibrin. Three plasminogen activators are currently available for converting plasminogen to plasmin: streptokinase, urokinase, and human tissue plasminogen activator (TPA). The term "thrombolytic agent" as used in this specification is therefore meant to include broadly any agent utilized for inducing or initiating the lysis of a thrombus. Other terms are known in the art for the lysis of a thrombus, including fibrinolysis. Although the most common thrombolytic agents are streptokinase, urokinase, and tissue-type plasminogen activator, any other thrombolytic agent can be utilized as defining the specificity of the relevant portion of the heterobifunctional antibodies of the invention.

Antibodies specific against thrombolytic agents may be raised according to means known in the art. In order to have enhanced specificity, it is preferred that monoclonal antibodies be raised against the thrombolytic agents. (Kohler and Milstein, *Nature* 256:49 (1975).

The process for obtaining a heterobifunctional antibody according to the present invention requires one antibody specific against a thrombus and the other antibody specific against a thrombolytic agent. These two antibodies may be modified by chemical procedures for preparing antibody fragments therefrom that can then be recombined to produce the heterobifunctional antibody. Alternatively, the heterobifunctional antibody can be prepared from the fusion of two hybridomas producing a hybrid hybridoma which secretes predefined heterobifunctional antibodies.

One procedure in which the anti-thrombus antibody and the anti-thrombolytic agent antibody may be chemically modified to produce the heterobifunctional antibody is described in Liu et al., *Proc. Natl. Acad. Sci. USA* 82:8648 (1985), incorporated herein by refecence. In this procedure, each antibody is treated separately with a molar excess of N-succinimidyl-3(2-pridyldithio)propionate (SPDP) dissolved in absolute ethanol. Thiol groups are then added to one of the modified antibodies by reacting a molar excess of 2-iminothiolanine dissolved in sodium borate. Then equal molar amounts of the two modified antibodies are mixed and after sufficient reaction time, the reaction is stopped by adding an excess of iodoacetamide. The reaction mixture is then passed over an affinity column to separate the bispecific antibody from uncoupled antibodies. In this procedure, the $F_c/F_{ab}$ one-half of the antibody molecule is kept intact.

In another chemical procedure for producing heterobifunctional antibodies, the $F_c$ fraction of the antibody is cleaved from the $F_{ab}$ fraction. This procedure is described in Brennan et al., *Science* 229:31 (1985), incorporated herein by reference. In this procedure, the $F_c$ portion of the antibody is cleaved by pepsin hydrolysis to yield the $F_{ab}$ portion. The $F_{ab}$ portion is then reduced by mercaptoethylamine in the presence of sodium arsenite to cleave the disulfide bond. The bonds are stabilized with Ellman's reagent, 5,5'-dithiobis(2-nitrobenzoic) acid. One of the stable $F_{ab}$ half-molecules is then treated with mercaptoethylamine and is mixed with an equimolar amount of the other untreated stable $F_{ab}$ half-molecule to form the heterobifunctional antibody. Advantages to utilizing $F_{ab}$ fragments is that the bispecific $(F_{ab})_2$ has a well-defined structure, is much smaller, and lacks the highly immunogenic $F_c$ portions of its component antibodies.

As used herein, the term "modification" refers to monospecific antibodies that are chemically altered, such as in the above two described procedures, to disassociate the antibodies and then reassociate them, producing the heterobifunctional antibody having dual specificity.

Alternatively, the heterobifunctional antibody may be produced by the fusion of hybridomas to produce a hybrid hybridoma that secretes predefined bispecific heterobifunctional antibodies. This procedure is described in Milstein and Cuello, *Nature* (London), 305:537 (1983), incorporated herein by reference. Methods for producing a hybrid hybridoma which secretes a hybrid monoclonal antibody having dual specificity against two different antigenic determinants is also described in PCT application, WO83/03679, also incorporated herein by reference. In the PCT application a procedure is described for using hybridomas with selectable markers, such that the monospecific hybridoma cannot survive in a medium in which the hybrid hybridoma is cultured. Thus, by the fusion of the two hybridomas, each conferring to the other the ability to grow in selected medium, the hybrid hybridoma can be easily selected. Examples of such selectivity include the inability to produce the enzyme HPRT, HAT-ouaban selection, HAT sensitivity, and antibiotic resistance.

The present invention also provides methods for immunotherapy and immunodiagnosis using heterobifunctional antibodies having a dual specificity, wherein one of the dual specificities is against a thrombus and the other specificity is against a thrombolytic agent. In the immunotherapeutic and immunodiagnostic applications, heterobifunctional antibodies produced from either chemical means or hybrid hybridomas can be used.

The heterobifunctional antibody of dual specificity can be used in immunotherapy by constructing it to have a specificity against a thrombus and a specificity against a thrombolytic agent. In the preferred embodiment of this invention, the anti-thrombus antibody is a monoclonal antibody against fibrin with substantially no cross-reactivity to fibrinogen and the thrombolytic agent is TPA. In this application, after the heterobifunctional antibody is administered to the patient, the heterobifunctional antibody then becomes localized at the site of the thrombus. During this time, the endogenous TPA will become attached to the heterobifunctional antibody.

Surprisingly, it has been found by the inventors that endogenous TPA is captured by the heterobifunctional antibody, enhancing the potency of endogenous TPA and fibrinolysis with increasing efficacy at decreasing concentrations of TPA (see example below). This method may also be used by first administering to the patient a low dosage of a thrombolytic agent. The heterobifunctional antibody is then administered to the patient, and it localizes at the site of the thrombus. The heterobifunctional antibody will capture the administered thrombolytic agent, directing it to the thrombus site. In results shown in in vitro testing, the heterobifunctional antibody may be first administered, followed by administration of a low dosage of the thrombolytic agent. As will be appreciated by one of skill in the art, the low dosage of the thrombolytic agent will reduce the risk of serious side effects, such as hemorrhage.

In another embodiment of this invention, the thrombolytic agent, for example streptokinase, urokinase, or TPA, is attached to the heterobifunctional antibody prior to administration to the patient. In this drug-targeted system, the specificity of the anti-thrombus portion of the heterobifunctional antibody permits selectivity of the antithrombolytic agent to lyse the thrombus. The heterobifunctional antibody may also be used in immunodiagnostic applications. In vivo immunodiagnosis can be performed using the heterobifunctional antibody of this invention. The heterobifunctional antibody, having one specificity against a thrombus and the second specificity against a thrombolytic agent, is first administered to the patient. After sufficient time has passed for the antibody to localize at the thrombus and unbound antibody has been permitted to clear from healthy tissue in the patient, the thrombolytic agent bearing a radionuclide is administered. The radionuclide must be of the type of decay which is detectable for a given type of instrument. Further, the radionuclide for in vivo diagnosis should have a half-life long enough that it is still detectable at the time of maximum uptake, but short enough that after diagnosis unwanted radiation does not remain in the patient. Coupling of the radionuclides to the protein agents is known in the art and is often accomplished either directly or indirectly using an intermediary functional group. Examples of radioisotopes that can be used for in vivo diagnosis are $^{99}Tc$, $^{123}I$, $^{131}I$, $^{111}In$, $^{97}Ru$, $^{67}Cu$, $^{67}TGa$, $^{68}Ga$, $^{72}As$, $^{89}Zr$, and $^{201}Tl$.

Paramagnetic isotopes for purposes of in vivo diagnosis can also be used according to the methods of this invention. Examples of elements that are particularly useful for use in Magnetic Resonance Energy techniques include $^{157}Gd$, $^{55}Mn$, $^{162}Dy$, $^{52}Cr$, and $^{56}Fe$.

The heterobifunctional antibody having dual specificity can further comprise a pharmaceutical composition, with a pharmaceutically acceptable carrier. These carriers are well known in the art and can include aqueous or solvent emulsions or suspensions, including saline and buffered media. The pharmaceutical compositions may be prepared by any of the methods that are well-known in the pharmaceutical art, for example, as described in *Remington's Pharmaceutical Sciences* (16th Edition, 1980).

The dose ranges for administration of the heterobifunctional antibody are those that are large enough to detect the presence of thrombi. The dosage should not be so large as to cause adverse side effects, such as unwanted cross rashes, and anaphylactic rashes and the like. Generally, the dosage will vary with the age, condition, sex, and extent of disease in the patient. Counter indications can include immune tolerance and other variables and can be adjusted by the individual physician. Dosage can range from 0.01 mg/kg to 500 mg/kg of body weight, preferably 0.01 mg/kg to 200 mg/kg. The heterobifunctional antibodies can be administered parentally by injection or by gradual perfusion over time. They can also be administered intravenously, intraperitoneally, intramuscularly, or subcutaneously.

Having now generally described this invention, the same will become more readily understood by reference to specific examples included herein for purposes of illustration only, and are not intended to be limiting unless otherwise specified.

EXAMPLES

Example 1

PREPARATION OF MONOCLONAL ANTIBODIES SPECIFIC FOR HUMAN TISSUE TYPE PLASMINOGEN ACTIVATOR (ANTI-tPA)

IgG1 mouse monoclonal antibodies specific for human tissue-type plasminogen activator (anti-TPA) were raised from A/J mice that had been immunized with human recombinant two-chain tissue-type plasminogen activator (TPA) (Genentech Inc). To select the appropriate clones, spleen cells from the immunized mice were fused with SP2/O myeloma cells and the mixture was then distributed into ten 96-well microtiter plates containing macrophage feeder layers. Hybridoma colonies were observed in over 95% of the wells. Supernatants from 12 wells showed evidence of anti-TPA binding in a solid phase immunoassay. The cloning and subcloning of these colonies by the limiting dilution method resulted in 33 stable lines, each producing anti-TPA antibody. Of these stable lines, 27 were IgG$_1$ Kappa and 6 were IgG$_{2b}$ Kappa as isotyped by the Boehringer kit. Two IgG$_1$ lines were selected for expansion in ascites and the antibodies subsequently purified by ammonium sulfate precipitation (45%) and DEAE-cellulose chromatography. The resulting antibody preparations were homogeneous by SDS-PAGE electrophoresis and demonstrated binding to the heavy chain of TPA by Western blotting. The apparent dissociation constants of the two anti-TPA antibodies was estimated by determining the half maximal binding concentration of $^{125}$I-TPA. One antibody was determined to have a $K_d$ of $4.5 \times 10^{-10}$ and the other $6.5 \times 10^{-10}$. Neither antibody inhibited the activity of TPA as measured either against an esterase substrate, S2444, or in a fibrinolysis assay against fibrin monomer (described in Example 3, below). The anti-TPA hybridoma cell line TCL8 was placed on deposit at the American Type Culture Collection (ATCC), Rockville, Maryland and designated ATCC No. HB9090. Hybridoma line TCL8 produces a monoclonal antibody specific for the catalytically active chain of TPA.

Example 2

PREPARATION OF HETEROBIFUNCTIONAL ANTIBODY HAVING DUAL SPECIFICITY FROM FIBRIN SPECIFIC MONOCLONAL ANTIBODY AND ANTI-TPA MONOCLONAL ANTIBODY

An IgG1 mouse monoclonal antibody specific for fibrin and not cross-reacting with fibrinogen (59D8) has been previously described in Hui et al., *Science* 222:1129–1131 (1983). Anti-TPA monoclonal antibody described in Example 1 was covalently coupled to antifibrin monoclonal antibody 59D8 utilizing the crosslinking reagent (N-succinimidyl 3-(2 pyridyldithio) propionate (SPDP). Lui et al., *Proc. Natl. Acad. Sci. USA* 82:8648–8652 (1985). In a typical experiment, 8.4 anti-fibrin antibody at a concentration of 2.4 mg/ml in 0.01M phosphate, 0.15M NaCl, 0.02% NaN$_3$, pH 7.4, (PBSA) was reacted with 50 ul of 20 mM SPDP in absolute ethanol. After 30 minutes at room temperature, the reagents were removed by gel filtration on a Sephadex G-25 column (2.5×30 cm) equilibrated with 0.14M NaCl, 1 mM KCl, 3.7 mM sodium phosphate, pH 7.4 (NaPi). A modification of from two to four 2-pyridyl-disulfide groups per more of anti-fibrin antibody was obtained. Grassetti et al., *Arch. Biochem. Biolchem. Biophys.* 119:41–49 (1967); Stuchbury et al., *Biochem. J.* 151:417–432 (1975).

Thiol groups were attached to the anti-TPA antibodies by reacting 8.4 mg of either of the two anti-TPA monoclonal antibodies at a concentration of 2.4 ng/ml in NaPi with a 200-fold molar excess of 2-imino-thiolane in 25 mM sodium borate, pH 9.1. After 45 minutes at room temperature, the mixture was fractionated on a Sephadex G-25 column (2.5×30 cm) equilibrated with 0.1M NaCl, 0.1M sodium phosphate, pH 6.6. This protocol introduces 1 to 2 thiol groups per antibody molecule. Lui et al., supra.

Equimolar amounts of the anti-fibrin and anti-TPA modified antibodies were mixed and stirred at room temperature for 3.5 hours. The reaction was then stopped by addition of 0.5 ml 1M iodoacetamide in 1M sodium phosphate, pH 8.0. At this point the mixture was no longer reactive with Ellman's reagent.

The sample was next concentrated to a volume of 9 ml in a 10 ml Amicon ultrafiltration cell using a YM 30 membrane and then applied to a calibrated Sephacryl S-300 column (2.5×85 cm) equilibrated with 0.1M phosphate, 0.1M NaCl, 1.0M urea, pH 6.6. Two peaks were clearly resolved. The first peak, eluting at approximately 300 Kd, was consistent with heterobifunctional antibodies (heterodimers). The second peak, eluting at 150 Kd, was presumed to contain unreacted antibody monomers. Small amounts of higher molecular weight materials were also observed, which were presumed to be higher polymers. The material from the 300 Kd peak was pooled and dialyzed against the buffer to be used in subsequent assays.

To bind TPA to the heterobifunctional antibody, 3.5 mg of TPA (0.5 mg/ml) was mixed with 5 mg of heterobifunctional ant i body (0.5 mg/ml) for 2 hours at room temperature. The solution was concentrated to a volume of 9 ml in a 10 ml Amicon ultrafiltration cell on a YM 30 membrane and applied to a Sephacryl S-300 column. Two peaks were resolved. One peak eluted with a slightly smaller volume than that of the heterobifunctional antibody peak, and with a molecular weight of approximately 400 Kd. Since the apparent molecular weight of TPA was 70 Kd on this column, the first peak was presumed to be an antibody-TPA complex and the second peak unbound TPA. On the basis of enzymatic activity (described in Example 3), it was estimated that about 1.5 moles of TPA were bound to each mole of heterobifunctional antibody.

Example 3

PEPTIDASE ENZYMATIC ACTIVITY ASSAY

The plasminogen-activating potency of TPA, the heterobifunctional fibrin-TPA antibody, urokinase, and a covalent complex of urokinase and a fibrin-specific antibody (urokinase-antibody conjugate) (Bode et al., *Science* 229:765–767

(1985)), were compared at equivalent peptidase activities. Peptidase activity independent of fibrin binding was measured with the chromogenic substrate, S-2288 (Helena Labs). Urokinase (Abbokinase, Abbot Lot #82-087-AF)) was the reference standard. The peptidase activity of 1 unit of urokinase was equal to that of 7 ng of TPA.

Example 4

PLASMINOGEN ACTIVATOR ASSAY

The lysis of $^{125}$I-fibrin monomer covalently linked to Sepharose 4B-Cl (fibrin-Sepharose) provided the end-point for the plasminogen-activator assay. Hui et al., supra. In this assay, the test substance was incubated with a 300 ul of a suspension of fibrin-Sepharose in a buffer containing 10 mM sodium phosphate, 0.1% BSA, 0.01% Tween-80, pH 7.4. The fibrin-Sepharose was washed with the same buffer and then incubated with 1 ml of plasminogen solution (0.15 mg/ml). Release of labeled peptides was measured at varyig intervals by counting aliquots of the supernatant after centrifugation of the fibrin-Sepharose and is expressed as a percentage of the total initial radioactivity.

The test substances assayed included:

i) the heterobifunctional antibody described in Example 2;

ii) the heterobifunctional antibody pretreated with TPA;

iii) TPA iv) urokinase (UK), and v) urokinase-anti-fibrin conjugate.

An additional sample, consisting of the heterobifunctional antibody that had been incubated with fibrin-Sepharose, washed, mixed with TPA, and washed again, was incubated with plasminogen as described above.

FIG. 1 shows that the concentration of TPA required to release labeled peptides from fibrin-Sepharose is about 1/10 that of urokinase and that the TPA heterobifunctional antibody is 10-fold more potent than TPA alone. There was no significant difference in fibrinolytic effectiveness between a heterobifunctional antibody that had been treated first with TPA and then added to the fibrin-Sepharose, and that of heterobifunctional antibody mixed first with fibrin-Sepharose and then treated with TPA. The TPA-heterobifunctional antibody is equipotent to the urokinase-anti-fibrin complex described in Bode et al., supra. The relative efficacy of TPA relative to urokinase has been attributed to the capacity of TPA to selectively bind to fibrin. Collen et al., Circulation, 70:1012–1017 (1984); Bergmann et al., Science 220:1181–1183 (1983); Hoylaerts et al., J. Biol. Chem. 257:2912–2919 (1982). Urokinase does not have a fibrin binding site. The even greater fibrinolytic potency observed with the TPA-heterobifunctional antibody, and with the urokinase-anti-fibrin complex, may be explained by the considerable difference in the relative affinity for fibrin that exists between TPA and fibrin-specific antibody 59D8. The $K_d$ of TPA for fibrin is 0.1 mM, whereas that of antibody 59D8 is approximately 0.1 micron. In the heterobifunctional antibody, the affinity of anti-TPA for TPA is 0.1 nM, not a limiting factor.

Example 5

TPA CAPTURE AT LOW CONCENTRATIONS

Figure 2:
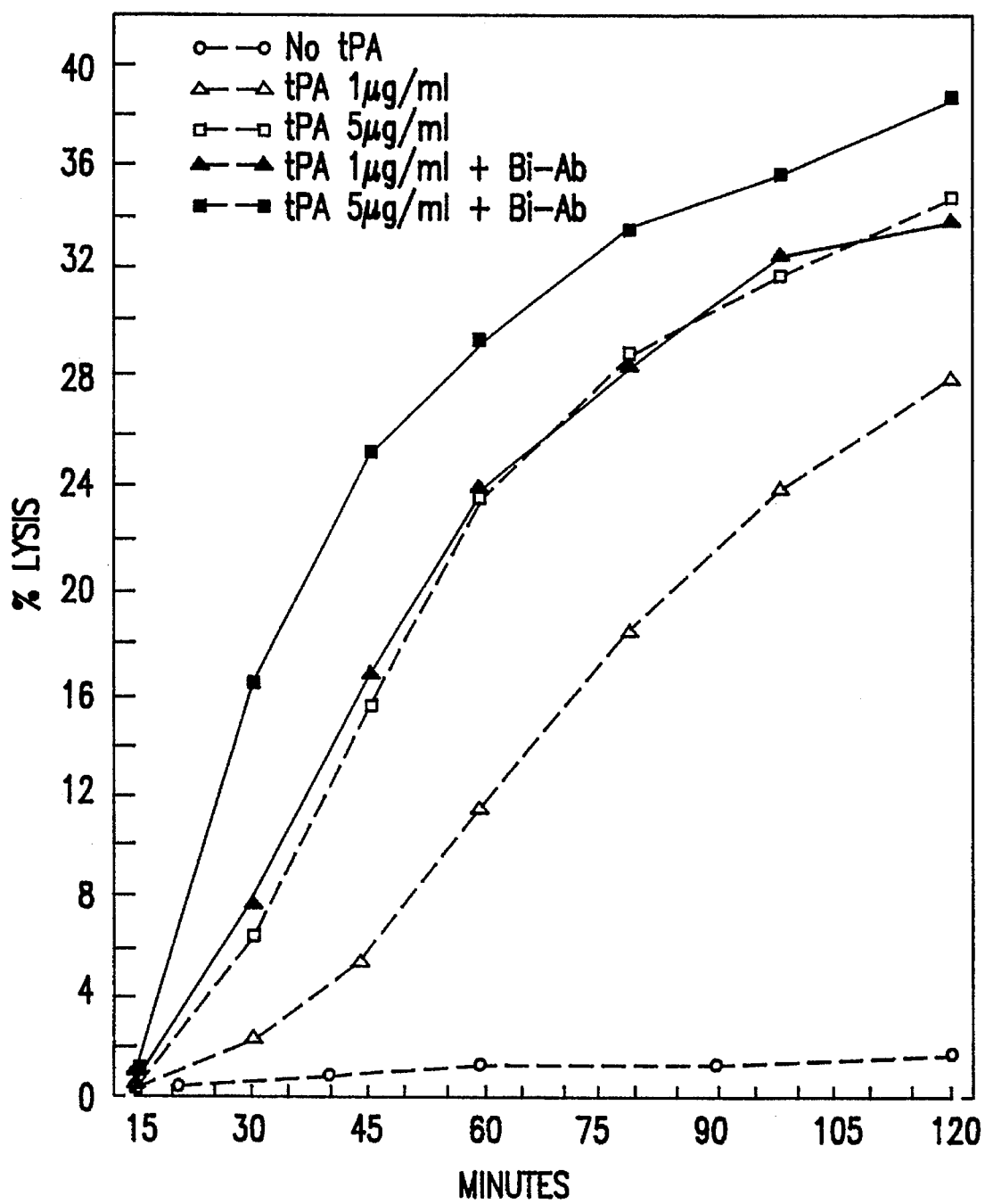
FIG. 2. The release of labeled peptides from fibrin-Sepharose (1) by TPA alone and (2) by TPA captured by a heterobifunctional antibody specific for both fibrin and TPA. For clarity, data at 0.1 and 0.34 ng/ml are not shown in this figure but are incorporated into FIG. 3. Each point represents the mean of three experiments with a mean standard deviation of 0.74.

The plasma concentration of TPA is reported to be in the range of 5 ng/ml. Hamster et. al., N. Engl. J. Med. 313:1557–63 (1985). To determine whether the fibrinolytic efficacy of TPA would be enhanced at these and lower TPA concentrations, 1 ml aliquots of fibrin-Sepharose were incubated both with or without 330 ug/ml heterobifunctional antibody in a volume of 1.0 ml for 4 hours at 20° C. A volume of 2.7 I of 100 mM phosphate, 0.1% BSA, 0.01% Tween-80 containing 0 (control), 0.1, 0.34, 1.0 or 5.0 ng/ml TPA was then run through a column at a flow rate of 180 ml/hr. After the fluid had passed through the column, the fibrin-Sepharose was removed and placed in a test tube at 25° C. One ml of plasminogen (0.15 1 mg/ml) was then added. The Sepharose was allowed to settle at the bottom of the test tube. At 20, 45, 60, 90, 120, 150 and 180 min, 0.6 ml of the supernatant solution was removed, counted in a gamma scintillation counter and then returned to the fibrin-Sepharose. Percent lysis was computed as the fraction of total counts released into the supernatant. FIG. 2 compares the fibrinolytic rates by TPA, both with and without pretreatment of fibrin-Sepharose with the heterobifunctional antibody. At each TPA concentration, the data indicate substantially enhanced fibrinolysis in the samples heated with heterobifunctional antibody.

Figure 3:
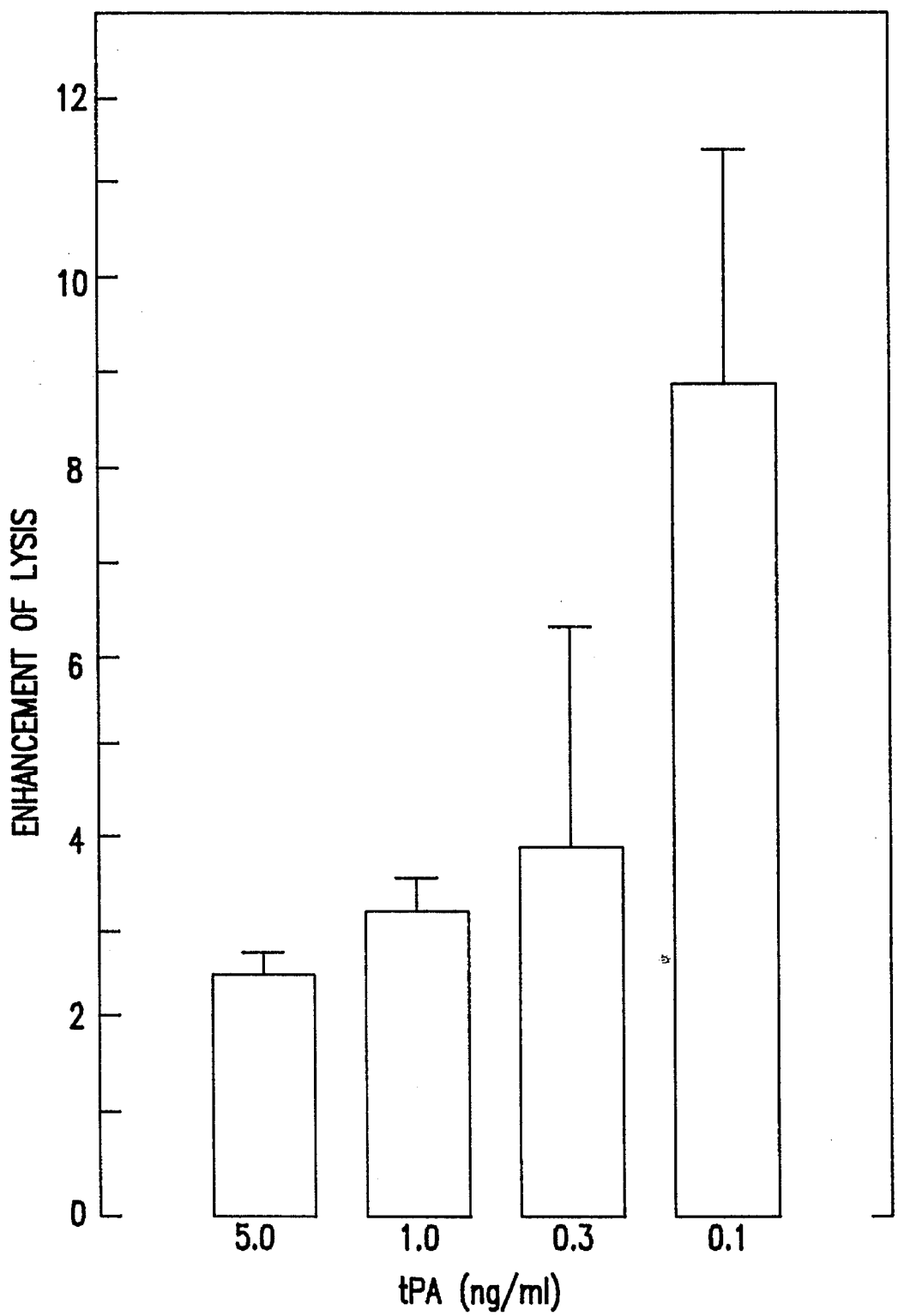
FIG. 3. The enhancement of fibrinolysis computed as the maximal quotient of percent lysis in the presence and absence of the heterobifunctional antibody. The data are taken from those shown in FIG. 2, with the addition of experiments at 0.1 and 0.34 ng/ml, not shown in FIG. 2. Error bars represent standard deviations of the mean of the quotient. This figure shows that the relative potency of TPA in the antibody-pretreated samples increases as TPA concentration decreases.

In FIG. 3, enhancement of lysis is defined as the ratio maximal of fibrinolysis in the presence and absence of heterobifunctional antibody. It is apparent that the relative potency of TPA-heterobifunctional antibody complex increases as TPA concentration decreases. This observation may be considered in light of the relative affinities of TPA and antibody for fibrin as discussed above. Anti-fibrin antibody has a higher affinity for fibrin than does TPA. The heterobifunctional antibody is consequently capable of binding TPA to fibrin with an affinity greater than that which could be effected by TPA alone.

Thus a heterobifunctional antibody composed of a fibrin-specific antibody and an anti-TPA antibody bound to fibrin enhances the fibrinolytic potency of TPA, with increasing efficacy at decreasing TPA. This phenomenon is readily demonstrable in vitro at or below TPA plasma concentrations. Extending these observations in vivo, the treatment of thrombosis may be without the administration of exogenous plasminogen activators. Since the affinity of fibrinspecific antibodies for fibrin is greater than that of TPA, the risk of fibrinogenolysis or of the destruction of other clotting proteins is minimized and thereby the risk of bleeding is likely to be diminished.

Example 6

The following example shows the production of two different heterobifunctional antibodies from somatic cell fusion of two hybridoma lines. The resulting cell lines secrete asymetic antibodies (heterobifunctional antibodies) capable of binding both fibrin and TPA and sharing with the chemically produced product the ability to enhance fibrinolysis. Both heterobifunctional antibodies contained a TPA binding site and an additional binding site: one antibody possessed an antibody binding site specific for the amino terminus of fibrin's beta chain (F36.23); the other antibody possessed an antibody binding site specific for the amino terminus of fibrin's alpha chain (F32.1).

ANTI-TPA, ANTI-BETA CHAIN HETEROBIFUNCTIONAL ANTIBODY

Hybridoma line TCL8 produces a monoclonal antibody specific for the catalytically active 8 chain of TPA. TCL8 cells were treated with 6-thioguanine to select for hypoxanthine phosphoribosyl transferase deficient (HPRT-MINUS) variants, subcloned and then tested for viability in HAT (hypoxanthine, aminopterin, thymidine)medium.

Hybridoma line 59D8, which produces a monoclonal antibody specific for the beta chain of human fibrin, was grown in bromodeoxy uridine in order to select thymidine kinase deficient subclones that were not viable in HAT medium. The HPRT-MINUS and the thyinidine kinase deficient subclones were fused in polyethylene glycol and desired clones selected that were viable in HAT medium. Further subclones were selected by screening with solid phase radioimmunoassay using a synthetic fibrin-like peptide and TPA as antigens. One cell line called F36.23 possessed both anti-human fibrin and anti-human TPA immunoreactivities. The products of this cell line were then purified to remove unproductive chain recombinants by serial affinity chromatography. Antibodies were first fractionated with beta chain peptide-Sepharose column and sequentially absorbed to and eluted from TPA-Sepharose. The purified products were then characterized by two additional assays that demonstrated their bifunctionality.

Figure 4:
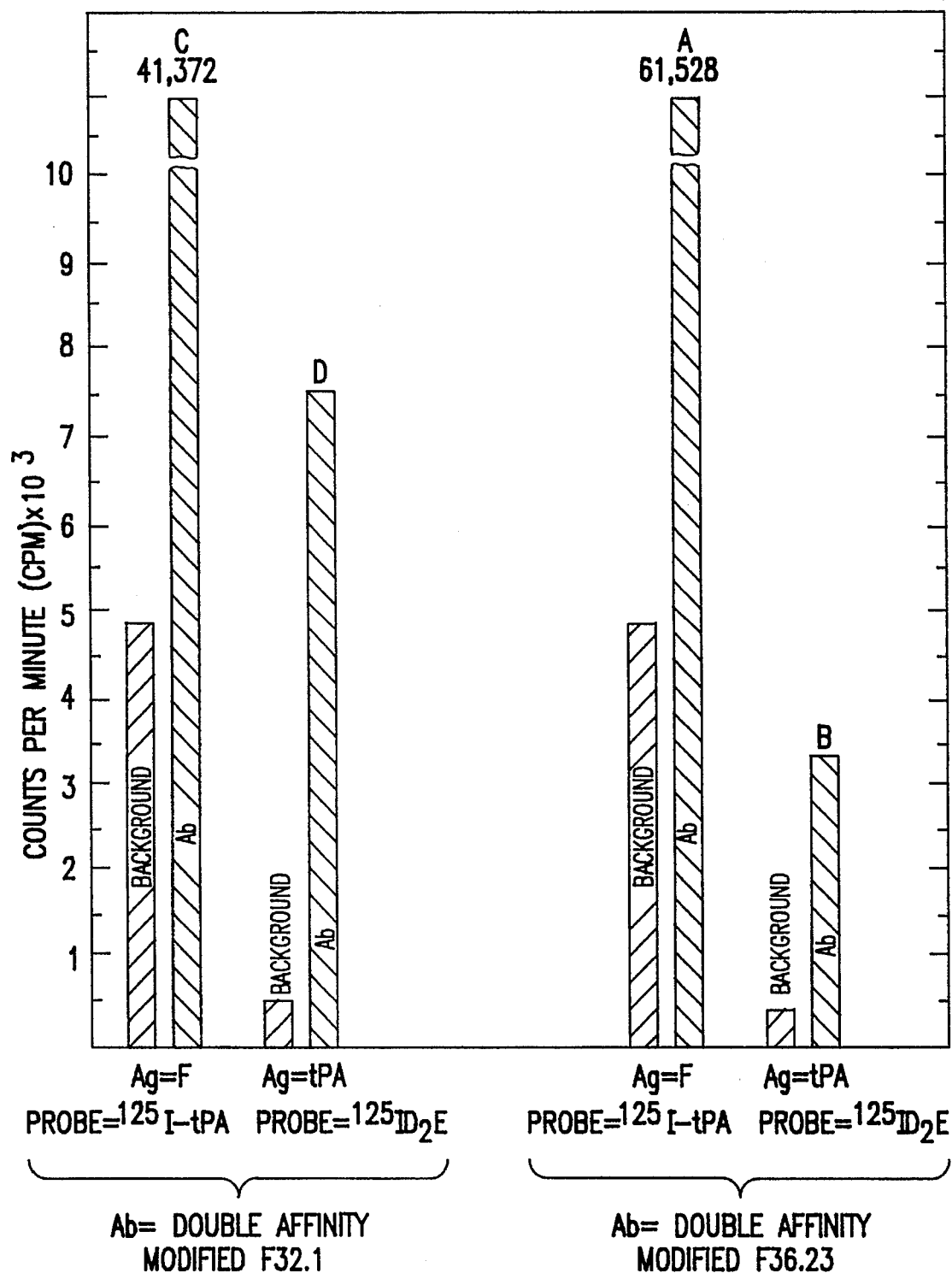
FIG. 4. The demonstration of antigen binding by heterobifunctional antibodies F32.1 and F36.23 produced by somatic fusion.

A solid-phase immunoradiometric assay was constricted in which fibrin monomer was adsorbed to a plastic surface, the test antibody solution added, followed by $^{125}I$ labeled tPA (with intervening washing steps). FIG. 4, column A shows evidence of binding to both fibrin and TPA. In FIG. 4, column 8, a similar assay was constructed in which TPA was adsorbed to the plate and $^{125}I$ labeled D2E (a fragment of fibrin containing that amino terminus of the beta and alpha chains) was the probe. Here too the binding by the test antibody compared favorably to the control. These assays indicate that the purified product of clone F36.23 is a heterobifunctional antibody capable of binding both fibrin and TPA.

ANTI-TPA, ANTI-ALPHA CHAIN HETEROBIFUNCTIONAL ANTIBODY

A second method was used to yield heterobifunctional antibody, F32.1. The F32.1 cell line was selected after fusing TCL8 (HPRT-MINUS) cells with spleen cells from a mouse immunized with a fibrin-like peptide corresponding to the amino terminus of fibrin alphachains. Fusion products were similarly screened using TPA and an alpha-chain peptide as antigens to yield the desired hybridoma which produced both activities. The isotype of this monoclonal antibody was Gammal, Kappa.

After affinity chromatography similar to that described for antibody F36.23, except that an amino terminal alpha chain peptide was used instead of the beta chain peptide, a similar immunoradiometric assay was performed. FIG. 4, column C, shows the binding of F32.1 when fibrin monomer is bound to the solid phase and $^{125}I$ tPA is the probe whereas FIG. 4, column D, shows the binding of the same antibody when TPA is bound to the solid phase and 125I D2E is the probe. These assays also indicate that the purified product of clone F32.1 is also a heterobifunctional antibody capable of binding both fibrin and TPA.

Figure 5:
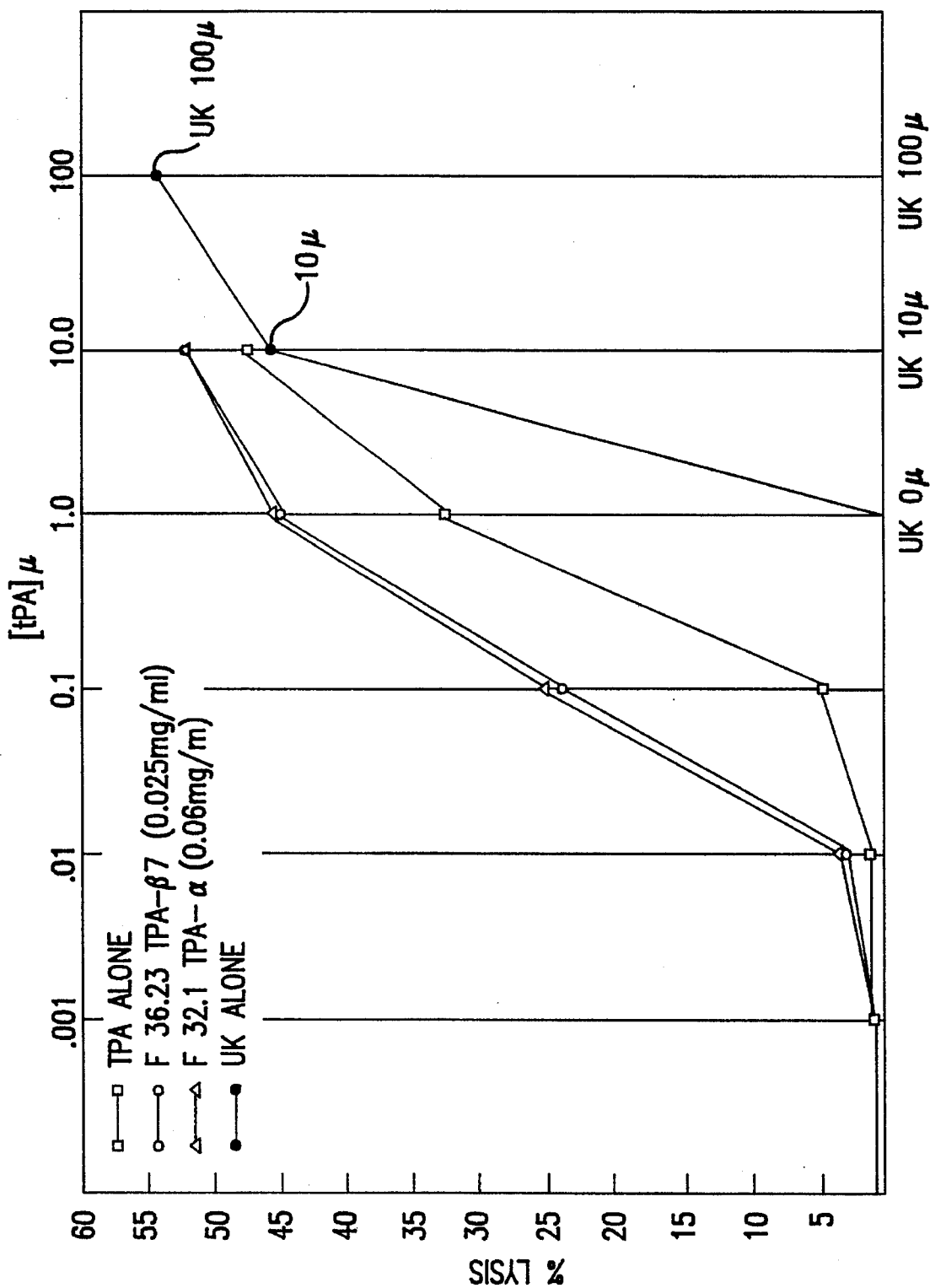
FIG. 5. The ability of the heterobifunctional antibodies F32.1 and F36.23 to enhance fibrinolysis.

Both antibodies were tested for their ability to enhance fibrinolysis in an assay previously described above and in Bode et al., Science 229:765–767 (1985). As is apparent from FIG. 5, the potency of TPA in fibrinolysis is enhanced five- to ten-fold by the presence of either F36.23 or F32.1.

Example 7

The following example describes the production and characterization of a heterobifunctional antibody assembled by linking an Fab' fragment from two antibodies, an antifibrin monoclonal antibody 59D8 and an anti-tPA monoclonal antibody TCL8. The bispecific (Fab')$_2$ enhances the fibrinolytic potency of tPA.

Experimental Procedures

The single-chain tPA used in these studies was derived from melanoma cells purchased from BioResponse (Hayward, Calif.). Two-chain, low molecular weight urokinase (Abbokinase) was purchased from Abbott Laboratories and Sepharose 4B-CL was obtained from Pharmacia P-L Biochemicals. The $^{125}I$-labeled fibrinogen came from Amersham, the plasma from the local blood bank. Chromogenic substrate H-D-isoleucyl-L-prolyl-L-arginine-p-nitroanilide dihydrochloride (S-2288) was obtained from Helena Laboratories. Human placenta factor XIII was purchased from Green Cross, Osaka, Japan, the Superose 12 resin for fast protein livid chromatography from Pharmacia. All other chemicals came from Sigma. Antibodies tPA-specific monoclonal antibody TCL8 and fibrin-specific monoclonal antibody 59DB were raised and purified as described (Bode, C., et al., J. Biol. Chem. 264:944–948 (1989); Hui, K. Y., et al., Science 222:1129–1132 (1983)).

Preparation of tPA-Sepharose

Twenty mg of one-chain recombinant tPA was solubilized in 10 mL of water and passed through a Sephadex G-25 column (30×2 cm) equilibrated with 0.2M NaHCO$_3$, 1.5M sodium chloride, and 0.1 percent Tween-80 (coupling buffer). The protein was immediately incubated with 15 mL cyanogen bromide-activated Sepharose (Pharmacia P-L Biochemicals) and coupled according to the manufacturer's instructions. After incubation for 24 h at 4° C., residual binding sites on the Sepharose were blocked with 10 mL of 1.0M ethanolamine (pH 8.0) for an additional 8 h.

Production and Purification of Bispecific (Fab')$_2$

The bispecific (Fab')$_2$ molecule was prepared by crosslinking the monovalent Fab's of antibodies 59DB and TCL8 (Brennan, M., et al., Science 229:81–83 (1985)). Each antibody was first digested with pepsin (Parham, P., J. Immunol. 131:2895–2902 (1983)): 10 mL of antibody solution (2.0 mg/mL in 0.01M sodium phosphate, 0.15M sodium chloride, pH 7.4) was mixed with I mL of 1.0M sodium citrate (pH 2.75) and 1 mL of pepsin solution (0.3 mg/mL in water), the final pH was adjusted to 3.5, and the mixture was incubated for 2 h at 37° C. The reactions were stopped by the addition of 1.0 mL of 3.0M Tris/HCl, pH 8.5. (Fab')$_2$ were then purified from the 59D8 and TCL8 digests by chromatography against their respective affinity ligands. For the former, β peptide (Gly-His-Arg-Pro-Leu-Asp-Lys-Cys, corresponding to the 7 amino-terminal residues of the β chain of fibrin) coupled to Sepharose (β peptide-Sepharose), for the latter, single-chain tPA coupled to Sepharose (see Preparation of tPA-Sepharose). After elution from the affinity matrices with 0.2M glycine (pH 2.8), each (Fab')$_2$ solution was collected into tubes containing a neutralizing amount of 3.0M Tris/HCl (pH 8.5), dialyzed into 0.1M sodium phosphate (pH 6.8), and reconcentrated in an ultrafiltration chamber to 2 mg/mL. Reduction of the 59D8 and TCL8 fragments was then carried out at room temperature in 1 mM 2-mercaptoethylamine, 1 mM ethylene diamine tetraacetic acid, and 10 mM sodium arsenite, followed by the addition of solid Ellman's reagent to a concentration of 5 mM. After 3 h at room temperature, excess reagent was removed from the two Fab' solutions by gel filtration on a Sephadex G-25 column (30×2 cm) equilibrated with 0.1M sodium phosphate (pH 6.8). The thiol form of antifibrin 59D8 Fab' was then regenerated by treatment with 10 mM 2-mercaptoethylamine for 30 min, followed by gel filtration as above. After that the antifibrin 59D8 Fab' was incubated with the thionitrobenzoate derivative of the anti-tPA TCLB Fab' for 16 h at room temperature in 0.1M sodium phosphate and 1 mM ethylene diamine tetraacetic acid (pH 6.8). The desired (Fab')$_2$ heterodimer was purified from the reaction mixture by sequential affinity chromatography on β peptide-Sepharose and tPA-Sepharose. The final yield of bispecific (Fab')$_2$ was 7 mg, or about 25 percent of the theoretical yield.

Preparation of Immunochemical Complex

An immunochemical complex made up of tPA and the bispecific (Fab')$_2$ [tPA-bispecific (Fab')$_2$ complex] was formed by mixing 3.5 mg of tPA (0.5 mg/mL) with 5 mg of bispecific (Fab')$_2$ (0.5 mg/mL) for 2 h at room temperature. After concentration to a volume of 9 mL, chromatography on Sephacryl S-300 revealed a peak of approximately 170 kDa [tPA bound to the bispecific (Fab')$_2$] and a second peak of approximately 70 kDa (unbound tPA). On the basis of enzymatic activity (assayed by S-2288), approximately one mole of tPA appeared to bind per mole of bispecific (Fab')$_2$.

Measurement of Plasminogen Activator Activity

To compare the activity of native tPA with that of tPA as part of an immunochemical complex, the amidolytic activities and molar amounts of tPA in the various preparations were measured in the following manner. Standardized samples of single-chain melanoma tPA or single-chain recombinant tPA (as aliquots from a freshly resuspended vial of tPA, in International Units) were analyzed in the S-2288 assay with a substrate concentration of $1 \times 10^{-3}$ mol/L and an enzyme concentration of $8 \times 10^{-9}$ mold in 0.15M Tris, 0.15M NaCl, pH 8.4. For tPA, 1 International Unit was assumed to equal $6.3 \times 10^{-5}$ nmol. The correlation between the reported change in absorbance/min for the assay preparations (Simoons, M. L., et al., *Lancet* 2:578–581 (1985)) and our samples was excellent, such that 100 units of single chain tPA ($6.3 \times 106$ mmol) gave an absorbance change at 405 nm of approximately 0.060/min. On the basis of these results, the activity (in appropriate units as above) or the molar amount of active enzyme of an unknown sample of urokinase or tPA was determined by diluting the sample until assay with S-2288 as described above produced an absorbance change of 0.060/min at 405 nm. The linear range of enzyme concentration to absorbance change was from $4 \times 10^{-9}$ mol/L to $3.2 \times 10^{-8}$ mol/L in our hands. If concentrations outside this range were used in any of the assays described here, appropriate dilutions were made from stock solutions that contained either $8 \times 10^{-9}$ mol/L or $8 \times 10^{-8}$ mol/L (an aliquot of which had been tested at a 1:10 dilution in the S-2288 assay).

Measurement of Fibrinolytic Potency

Relative fibrinolytic potency was quantified by measuring the lysis of $^{125}$I-labeled fibrin monomer covalently linked to cyanogen bromide-activated Sepharose 4B-C1 (quantitative fibrinolysis assay) (Bode, C., et al., *Science* 229:765–767 (1985)). To facilitate direct statistical comparison between fibrinolysis with a plasminogen activator alone and fibrinolysis with a plasminogen activator in the presence of the bispecific antibody, a Fit-Function Program (BBN Research Systems, *RS/1 User's Guide*, Book 2, Release 2, Serial V-14342, pp. 180–187, Bolt Beranek and Newmann, Cambridge, Mass. (1983)) was applied to the data from each assay and the curves were compared by the t test, as previously described (Bode, C., et al., *J. Mol. Cell. Cardiol.* 19:335–341 (1987)).

Results

Figure 6A:
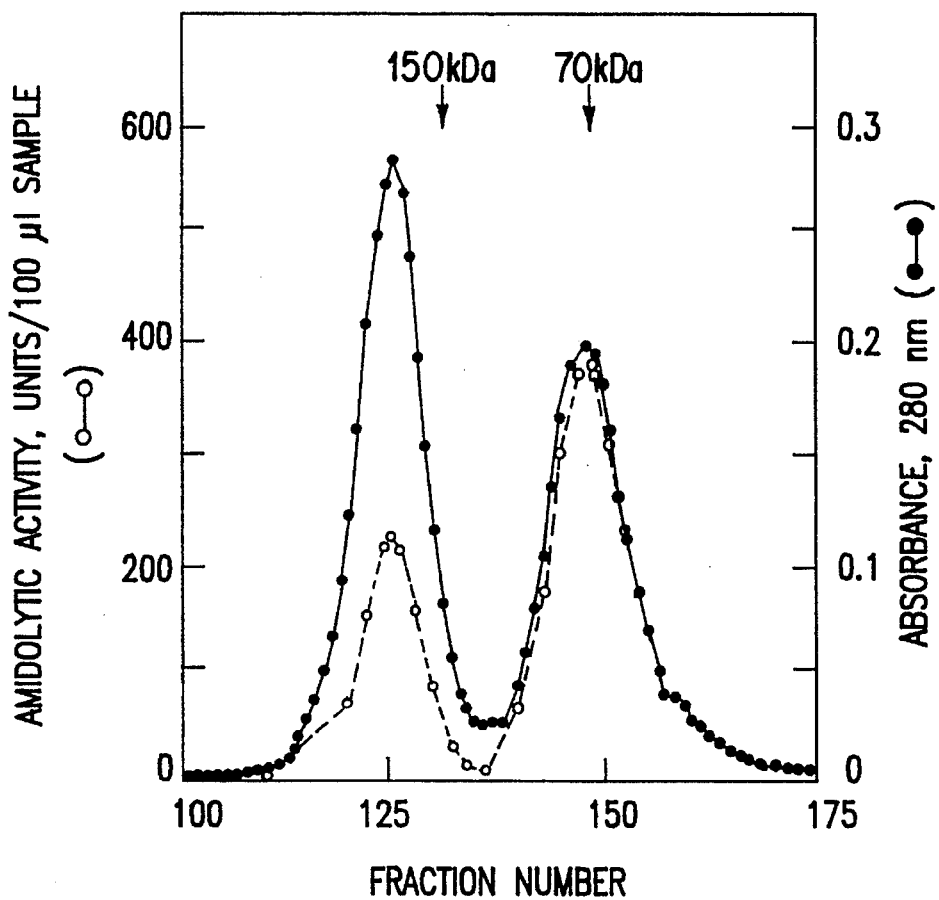
FIGS. 6A and 6B. Gel filtration on a calibrated Sephacryl S-300 column of the tPA-bispecific (Fab')$_2$ complex. A, the gel filtration resulted in two protein peaks, both of which contained enzymatic activity. Profiles of absorbance at 280 nm (closed circles) and amidolytic activity (open circles) are shown. On the basis of molecular weights and the relative specific enzymatic activities of the two peaks (B), peak 1 (170 kDa) was judged to contain a 1:1 molar conjugate of bispecific (Fab')$_2$ and tPA and peak 2 was judged to contain unbound tPA.
Figure 6B:
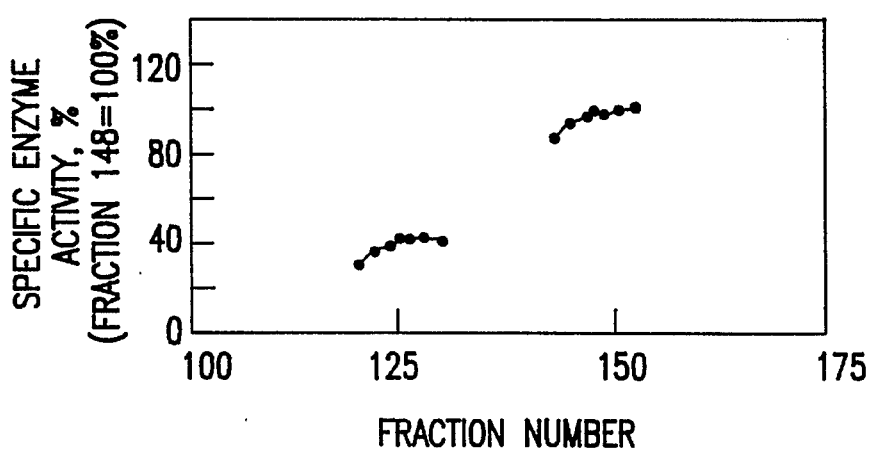

FIG. 6A shows the characterization of the tPA-bispecific (Fab')$_2$ complex on a calibrated Sephacryl S-300 column. The first peak eluted at an apparent molecular size slightly higher than 150 kDa (IgG was used as marker protein), which corresponds to the presumed size (170 kDa) of an immunochemical complex made up of the heterodimer (Fab')$_2$ and tPA. The second peak eluted at 70 kDa, corresponding to single-chain recombinant tPA. Both peaks contained enzymatic activity, as assessed by the S-2288 chromogenic substrate assay. The calculated theoretical specific activity of a 1:1 complex of bispecific (Fab')$_2$ and tPA is 41.6 percent of the specific activity of tPA alone. FIG. 6B shows that the specific enzymatic activity of fractions from Peak 1 was about 40 percent that of the fractions from Peak 2.

Figure 7A:
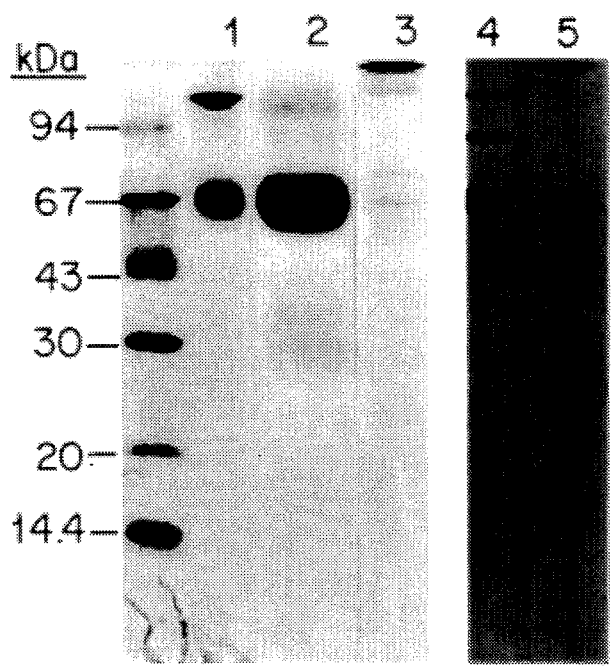
FIGS. 7A and 7B. SDS-PAGE of tPA-bispecific (Fab')$_2$ complex. Ten percent polyacrylamide gels were run under nonreducing (panel A) and reducing (panel B) conditions. A) numbers on the left correspond to molecular weight standards (Pharmacia): Lane 1, tPA-bispecific (Fab')$_2$ complex; Lane 2, one-chain recombinant tPA; Lane 3, antifibrin 59D8 (Fab')$_2$; Lane 4, anti-tPA TCL8 (Fab')$_2$; and Lane 5, anti-tPA antibody. B) Lans 1–5 as in A.
Figure 7B:
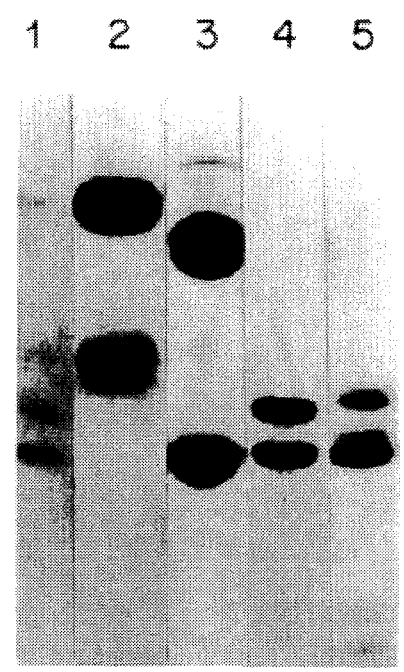

The results of SDS-PAGE on the first fraction in FIG. 6A are shown in FIG. 7. Under nonreducing conditions (Panel A), the tPA-bispecific (Fab')$_2$ complex displayed two bands: one corresponding to the size of an (Fab')$_2$ molecule, the other to the size of a tPA molecule. Under reducing conditions (Panel B), bands corresponding in size to the two chains of the Fab' molecules and to one-chain tPA could be seen, and there was evidence of traces of two-chain tPA.

Figure 8:
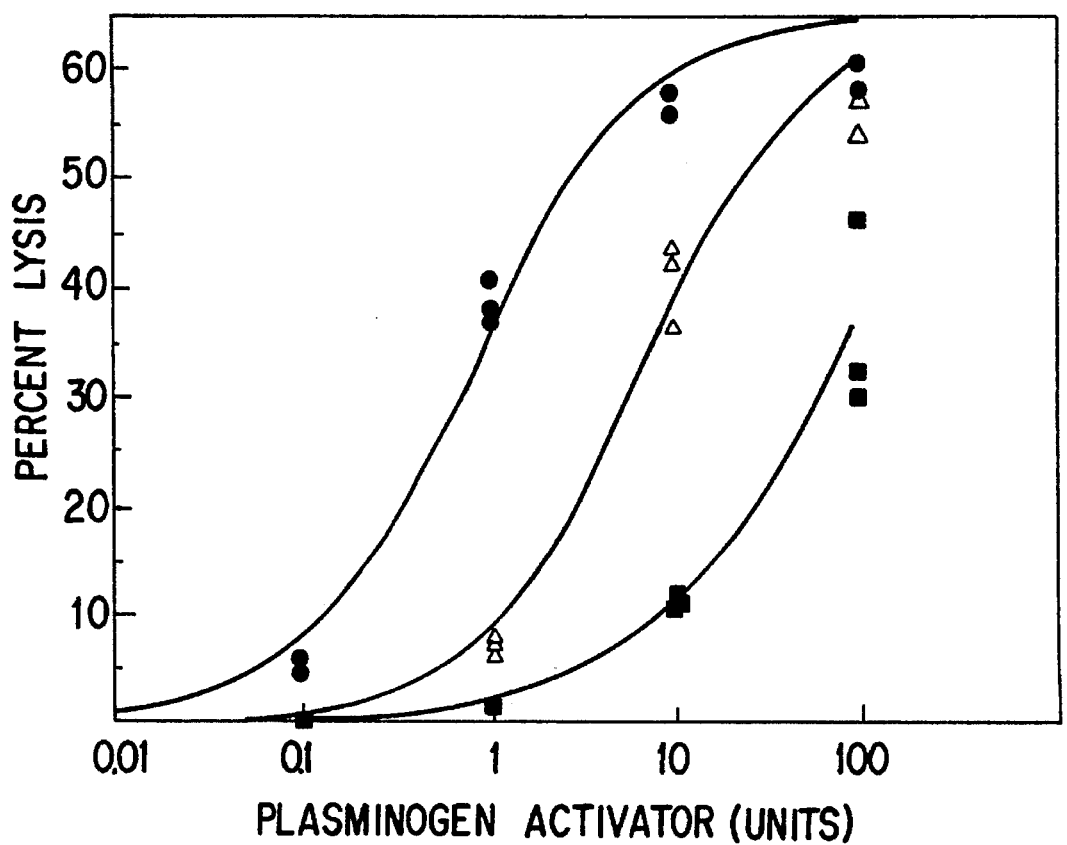
FIG. 8. Release of radioactive peptides from $^{125}$I-labeled fibrin-Sepharose by the tPA-bispecific (Fab')$_2$ complex (filled circle); by tPA alone (open triangle); and by urokinase alone (filled square). Lysis is expressed as the quotient of released radioactivity over total radioactivity. Each point represents the mean of three determinations. A 3-parameter inverse logit function was used to fit the curves to the original triplicate points.

The tPA-bispecific (Fab')$_2$ complex was compared with tPA alone and with urokinase in the quantitative fibrinolysis assay (FIG. 8). In these experiments, the tPA-bispecific (Fab')$_2$ complex was 8.6-fold more efficient in fibrinolysis than tPA alone (p<0.0001), and 94-fold more potent than urokinase (p<0.0001). Here tPA was 11-fold more efficient than urokinase, a finding similar to that of previous experiments (Bode, C., et al., *J. Biol. Chem.* 264:944–948 (1989)). It is of particular interest that the tPA-bispecific (Fab')$_2$ complex showed an enhancement in the fibrinolytic activity of tPA similar to that of the tPA-bispecific antibody complex (Bode, C., et al., *J. Biol. Chem.* 264:944–948 (1989)).

Discussion

Here we describe a bispecific (Fab')$_2$ that has affinity for both fibrin and tPA. The rationale for producing this bispecific (Fab')$_2$ was based on promising results obtained when intact anti-fibrin and anti-tPA antibodies were coupled. We previously demonstrated (Bode, C., et al., *J. Biol. Chem.* 264:944–948 (1989); Runge, M. S., et al., *Trans. Assoc. Am. Phys.* 100:250–255 (1987); Runge, M. S., et al., *Clin. Res.* 56:501–506 (1988)) that a bispecific antibody containing intact antifibrin and anti-tPA antibodies is capable of concentrating tPA and enhancing the fibrinolytic potency of tPA in vitro, in human plasma, and in vivo in the rabbit jugular vein model. In model experiments, the bispecific antibody was able to concentrate the low amounts of tPA normally present in human plasma and effect fibrinolysis. This increased potency is probably related to the fact that the antifibrin antibody has an affinity for fibrin 1800 times greater than that of tPA: the $K_D$ of tPA for fibrin is $0.14 \times 10^{-6}$M (Hoylaerts, M., et al, *J. Biol. Chem.* 257:2912–2919 (1982)), whereas that of antibody 59D8 is $0.77 \times 10^{-10}$M. However, one limitation to the clinical utility of the bispecific whole antibody is that the coupling chemistry used to create it does not yield a homogeneous product.

The bispecific (Fab')$_2$ is a better-defined molecule than the bispecific whole antibody because the linkage between the component Fab's in the fragment antibody occurs only at the disulfide bonds of the hinge region. Thus only those molecules that possess both fibrin and tPA binding properties would remain after sequential affinity chromatography against the two antigens. The gel filtration data presented in FIG. 7 suggest that tPA binds to the bispecific (Fab')$_2$ in a 1:1 complex. Our calculations indicate that almost all the bispecific (Fab')$_2$ reacted with the tPA. This suggests that the purification process selects for functionally active molecules. The ability of the bispecific (Fab')$_2$ to enhance the fibrinolytic potency of tPA is apparently identical to that of the bispecific whole antibody. Thus monovalent binding to both antigens appears to be sufficient to effect increased potency. The smaller bispecific (Fab')$_2$, as opposed to the bispecific whole antibody, may provide advantages for later in vivo studies and, more importantly, can be synthesized in a reproducible manner that does not require the introduction of cross-linking reagents, which have the potential to act as immunogenic epitopes.

Example 8

The following example describes the production and characterization of bispecific antibodies by somatic cell fusion. Two bispecific monoclonal antibodies and their corresponding F(ab')$_2$—one a hybrid hybridoma, the other a hybridoma—bind simultaneously to fibrin and tPA and target tPA to fibrin in vitro and in vivo.

Materials

Keyhole limpet hemocyanin was obtained from Calbiochem (La Jolla, Calif.). Standard tissue culture medium (Dulbecco's Modified Eaglets Medium; Biofluids, Rockville, Md.) contained 13% (v/v) fetal bovine serum for hybridomas and 50/µg/ml gentamicin (each obtained from Whittaker Bioproducts, Walkersville, Md.). Selective growth medium contained hypoxanthine, aminopterin, and thymidine (HAT; Sigma, St. Louis, Mo.). 5-Bromo-2'-deoxyuridine and 2-amino-6-purinethiol (6-thioguanine) were obtained from Aldrich Chemical (Milwaukee, Wis.), and polyethylene glycol (EM grade, MW 4000) was obtained from E. Merck (Darmstadt, Federal Republic of Germany). Heparin (1000 units/ml) was purchased from Elkins-Sinn (Cherry Hill, N.J.), human fibrinogen from Kabi (Stockholm, Sweden). Thrombin (bovine, 1000 units/ml) was obtained from Parke-Davis (Morris Plains, N.J.). The mouse immunoglobulin subtype identification kit was from Boehringer Mannheim (Indianapolis, Ind.). Microtiter plates (96 well), culture plates (24 well), and polyvinylchloride plates used for radioimmunoassay (RIA) were obtained from Falcon/Becton Dickinson (Lincoln Park, N.J.). Amino acid analysis was performed in a Durrum (Sunnyvale, Calif.) 500 apparatus.

Factor XIII (human placenta) was obtained from Green Cross, Osaka (Japan). Plasmin (0.188 mg/ml in water), aprotinin (0.022 TIU/ml), ethylene diamine tetraacetic acid, iodoacetamide, Tween-80, and phenylmethyl sulfonyl fluoride were purchased from Sigma. Superose 12 resin from Pharmacia (Piscataway, N.J.) was used for fast protein liquid chromatography, and IgG-depleted horse serum from GIBCO/BRL Life Technologies (Gaithersburg, Md.) was used for blocking solutions. Single-chain human recombinant tPA was obtained from Genentech (South San Francisco, Calif.), melanoma-derived tPA (m-tPA) from Bio Response (Hayward, Calif.). D-isoleucyl-L-prolyl-L-arginine-p-nitroanilide (S-2288), a chromogenic substrate for peptidase activity, was purchased from Helena Laboratories (Beaumont, Tex.). Polyacrylamide gel electrophoresis materials and molecular weight standards were obtained from Bio-Rad Laboratories (Richmond, Calif.). Affinity-purified goat antimouse F(ab')$_2$ (GAMF$_{ab}$; Cappel Laboratories, West Chester, Pa. was iodinated according to the chloramine-T method (Hui, K. Y., et al., Science 222:1129–1132 (1983)). $^{125}$I-labeled fibrinogen and $^{125}$I-labeled Na$_2$ were purchased from Amersham (Arlington Heights, Ill.). In RIA and fibrinolysis assays, gamma emission was measured with a Micromedic Systems (Horsham, Pa. Model 4/600 Gamma Counter. Iodination was measured with a RADX (Houston, Tex.) Mark V Isotope Dosecalibrator.

P-methyl benzhydrylamine HCl resin (1.2 mec/g substitution; United States Biochemical, Cleveland, Ohio) was used for solid-phase peptide synthesis. Cyanogen bromide-activated Sepharose 4B-CL and w-aminohexyl-Sepharose 4B were obtained from Sigma.

Methods

HYBRID-HYBRIDOMA BISPECIFIC ANTIBODY F36.23

Production: Drug Marking and Fusion

59D8 cells (secreting a monoclonal antibody that is specific for the fibrin chain and that does not react with fibrinogen (Hui, K. Y., et al., Science 222:1129–32 (1983)) and TCL8 cells (producing an antibody specific for the light (B) chain of human tPA) were established in tissue culture as previously described (Bode, C., et al., J. Biol. Chem. 264: 944–8 (1989)). 59D8 cells were rendered thymidine kinase deficient (TK$^-$) by incubation for three weeks in culture medium containing 5-bromo-2'-deoxyuridine (30 µg/ml). TCL8 cells were rendered hypoxanthine guanine phosphoribosyl transferase deficient (HGPRT$^-$) by incubation for three weeks in culture medium containing 6-thioguanine (6 µg/ml). Each line was subcloned at limiting dilution (0.5 cells/well) and the subclones were tested for viability in HAT medium. Subclones sensitive to HAT medium were selected for fusion.

Polyethylene glycol-mediated cell fusions were performed according to the method of Köhler and Milstein (Köhler, G., et al., Nature (London) 256:495–7 (1975)), with some modifications. TK$^-$ 59DB cells and HGPRT$^-$ TCL8 cells were fused in equal parts. The cells were applied to 96-well microtiter plates (at 5000 and 1000 cells per well). After growth for 5 days in conditioned medium (Hui, K. Y., et al., Science 222:1129–32 (1983)), 100 µl of supernatant was replaced with HAT medium and the cells were tested for antifibrin and anti-tPA activities.

Radioimmunnoassay to Confirm Bispecificity for Fibrin and tPA 96-well polyvinylchloride microtiter plates were coated with 25 µl of β peptide (Gly-His-Arg-Pro-Leu-Asp-Lys-Cys, which had been used to raise antibody 59D8) or fibrin monomer, or with tPA (each at 0.01 mg/ml). Control plates were coated with 25 µl of 10% horse serum (HS). After 2 h at room temperature (or overnight at 4° C.), the plates were washed with distilled water. Wells were then filled with blocking solution (10% HS with 20 units of heparin/ml, phenylmethyl sulforyl fluoride (174 mg/ml), and aprotinin (10 µl/ml (v/v) in phosphate buffered saline azide, PBSA) and were incubated for 30 min at room temperature, after which they were washed with distilled water. Culture supernatant or purified antibodies (25 µl) was added to each well and incubated for 2 h at room temperature. The plates were again washed with distilled water. Finally, 25-µl aliquots of $^{125}$I-labeled goat antimouse F(ab')$_2$ probe (50000–75000 cpm/25 µl, radioiodinated according to the chloramine-T method (Greenwood, F. C., et al., Biochem. J. 89:114–23 (1963))) were added to each well and incubated for 1 h at room temperature. The plates were washed extensively with tap water and gamma emission was measured.

Purification by Affinity Chromatography

β peptide-Sepharose affinity resin was prepared with bromoacetyl N-hydroxy succinimide and chromatography was performed as described (Bode, C., et al., Science 229:765–7 (1985)). tPA-Sepharose affinity resin was made according to the manufacturer's specifications, with cyanogen bromide-activated Sepharose 4B-CL (4 ml of swelled resin per 40 mg of tPA) and m-tPA). The resin was incubated with 0.5M ethanolamine (pH 8.0) before the first use, and washed with 0.2M glycine (pH 2.8) before each subsequent use. The total binding capacity of the two affinity resins was determined with purified monospecific antibody. A benzamidine-Sepharose 4B-CL imuunoabsorbent resin was prepared, and was also washed with 0.2M glycine (pH 2.8) before each use.

Amplification in Ascites

CAF/J mice were injected with hybridoma line F36.23 ten days after they had been primed with pristane by intraperitoneal injection. Ascites was collected into a heparin solution (final concentration 250 units/ml). Aliquots of ascites were clarified by sterile filtration (through 0.45-μM syringe-tip filters) and purified on the β peptide-Sepharose column. The column was washed with PBSA until the absorbance of the effluent was less than 0.05 at 280 nm. Nonspecifically bound antibodies were eluted with 3M KCl in PB5A and discarded. Fibrin-specific antibodies were eluted with 0.2M glycine (pH 2.8) and the pH was immediately neutralized with 3M Tris (pH 8.6). The eluate from the β peptide-Sepharose column was then subjected to affinity chromatography on a tPA-Sepharose column.

The amount of antibody possessing both antifibrin and anti-tPA activities was measured as follows. Clarified ascites was precipitated with 45% $(NH_4)_2SO_4$ for 4 h with stirring on ice, and then allowed to stand overnight at 4° C. After centrifugation for 20 min at 10000 rpm, the pellet (largely containing gamma globulin) was dissolved in distilled water and dialyzed against PBSA. To test for antifibrin activity, small aliquots (less than 10% of the binding capacity of the β peptide-Sepharose affinity resin) were absorbed on the resin and eluted. The percentage of total gamma globulin that bound to the β peptide-Sepharose was then calculated. To test for anti-tPA activity, the percentage of total gamma globulin that bound to the tPA-Sepharose column was calculated. The percentage of total gamma globulin that was bispecific was determined by taking the eluted fraction from either the β peptide-Sepharose or tPA-Sepharose column and measuring the binding to tPA-Sepharose or β peptide-Sepharose, respectively. Nonsaturating amounts of 59DB and TCL8 parental antibodies were absorbed on the β peptide-Sepharose and tPA-Sepharose columns, respectively, and the percent binding of monospecific antibodies was calculated.

Characterization: Isotyping and Sequencing

Antibody was adsorbed to polyvinylchloride wells coated with β peptide or tPA as described above. Isotype was determined by enzyme-linked immunoassay according to the manufacturer's protocol and with the accompanying reagents. The N-terminal amino acids of purified 59DB (10 residues), TCL8 (21 residues), and F36.23 (10 residues) were sequenced on an Applied Biosystems (Foster City, Calif.) 470A Protein Sequencer. High performance liquid chromatography was performed in an Applied Biosystems 120A PTH apparatus Analyzer and the data was analyzed with an on-line Shimadzu (Columbia, Md.) C-R3A Chromatopac Integrator.

Preparation of Fibrin Fragment D2E

Human fibrinogen (50 mg) was dissolved in distilled water and passed through a 0.45-micron filter into a solution of 5 ml Tris buffer (0.1M, pH 7.4) with 0.1M NaCl, 0.02% sodium azide, 37.5 μl $CaCl_2$ (2M), 5 μl thrombin, and 100 μl Factor XIII. After 2 h, 1 ml of plasmin was added and the clot was incubated overnight at 37° C. Supernatant was filtered through a 0.45-micron filter and 0.5 ml of aprotinin was added. D2E was purified by fast protein liquid chromatography and the major peak (corresponding to 215 kD) was collected. Diluted D2E was stored in 1M sodium bromide with 0.05M sodium acetate, pH 5.3.

Preparation of Fibrin Monomer

Fibrin monomer was prepared from human fibrinogen as described (Hui, K. Y., et al., *Science* 222:1129–32 (1983)), with the following modifications. Fibrinogen (60 mg) was dissolved in 4 ml of iodoacetamide (4 mg/ml) and passed through a 0.45-micron filter. Bovine thrombin (1000 units/ml) in an equal volume of potassium phosphate buffer (100 mM, pH 7.0) containing ethylene diamine tetraacetic acid (50 mM) and aprotinin (0.0022 TIU) was added. The resulting clot was blotted on filter paper and washed 4 times with 10 ml of PBSA containing 0.1 mM phenylmethyl sulfonyl fluoride. The clot was solubilized in a 1-M sodium bromide solution in 0.05M sodium acetate buffer, pH 5.3.

Radioimmunoassays to Assess Dual Specificity

Radioimmunoassays were developed to determine simultaneous binding. m-tPA and fibrin fragment D2E were radioiodinated according to the chloramine-T method. In one assay, fibrin monomer was used as fixed antigen and $^{125}$I-labeled tPA was used as probe. In a complementary assay, tPA was used as fixed antigen and $^{125}$I-labeled D2E was used as probe (because fibrin monomer does not reproducibly stay in solution at the appropriate concentrations). A 25-μl aliquot of antigen (0.01 mg/ml) was adsorbed to polyvinylchloride microtiter wells for 2 h at room temperature. Wells used to determine nonspecific binding received no initial antigen. The plates were washed with distilled water and blocked with 10% HS solution for 30 min at room temperature. Aliquots of affinity-purified antibody (25 μl, 0.05 mg/ml in PBSA with 5% HS blocking solution) were then added to the wells and incubated for 2 h at room temperature. The plates were washed with distilled water. Each probe was diluted to 160,000 cpm/25 μl with PBSA containing 5% HS solution and 0.1% Tween-80. Finally, 25-μl aliquots of probe were incubated with the wells for one h at room temperature. The plates were washed with tap water and gamma emission was measured.

Preparation of F(ab')$_2$ Fragment

Bispecific antibody F36.23 was digested with pepsin, as described by Parham (Parham, P., *J. Immunol.* 131:2895–2902 (1983)). Digestion conditions were determined in pilot experiments in which the bispecific antibody was digested with pepsin for 0.5, 1.0, 2.0, 3.0, 4.0 and 5.0 h, and the results were monitored by sodium dodecyl sulfate polyacrylamide gel electrophoresis under nonreducing conditions, as described (Laemmli, U.K., *Nature* (London) 227:680–685 (1970)).

Preparation of Bispecific Antibody-tPA Immunoconjugate

Affinity-purified F36.23 was incubated with m-tPA in a 20:1 molar ratio, with slow stirring for 2 h at 4° C. The preparation was chromatographed on a benzamidine-Sepharose column as described (Bode, C., et al., *J. Biol. Chem.* 264:944–948 (1989)), and, after elution and pH neutralization, the amidolytic activity of the F36.23 immunoconjugate was measured in an S-2288 assay (Bode, C., et al., *J. Biol. Chem.* 264:944–948 (1989)). A duplicate sample was chromatographed on a β peptide-Sepharose column and the amidolytic activity of the eluted sample was also measured.

Assay for the Lysis of Human Fibrin Monomer $^{125}$I-labeled fibrin-Sepharose was prepared and fibrinolysis with tPA was assayed as described (Bode, C., et al., *Science* 229:765–767 (1985)). The amidolytic activities of m-tPA and the F36.23 tPA immunoconjugate were calibrated immediately before use by assay with S-2288. The concentration of bispecific antibody that would be used in final assays was determined by comparing potencies over a broad range of concentrations. (For the experiments described here, fibrinolysis with 0.1 unit of tPA was measured alone and with 100 μl of bispecific antibody F36.23 at 0.4 mg/ml, and over a dilution series.) Maximal enhancement was observed at 2.5/μg/100 μl of F36.23. Fibrinolysis was determined for concentrations of tPA ranging from 0.01 to 100 units/ml, with tPA alone, with tPA and bispecific antibody F36.23 added separately, and with tPA as contained in the F36.23-tPA immunoconjugate.

In Vivo Thrombolysis Model

The rabbit jugular vein model of Collen et al. (Collen, D., et al., *J. Clin. Invest.* 71:368–376 (1983)) was used, with modification (Runge, M. S., et al., *Proc. Natl. Acad. Sci. USA* 84:7659–7662 (1987)). In the experiments reported here, 2 mg/kg of bispecific antibody was mixed with the designated amount of tPA (either 0.5 mg/kg or 0.25 mg/kg) just before infusion through the contralateral marginal ear vein over 4 h. In control experiments, 2 mg/kg of TCL8 was mixed with tPA just befoe infusion. Rabbits were also treated with various concentrations of tPA or saline (to measure background lysis), as described (Runge, M. S., et al., *Proc. Natl. Acad. Sci. USA* 84:7659–7662 (1987)). After the 4-h infusion of test substance, saline as infused for 1 h, after which the rabbit was killed by infusion of KCl. The amount of radioactivity remaining in the jugular vein segment was determined by gamma counting.

Fibrinogen Assays

The fibrinogen content of samples of citrated human plasma or citrated rabbit plasma was determined by two methods. Clottable fibrinogen was measured by the method of Clauss et al. (*Acta Haematol.* 17:237–246 (1957)), and total fibrinogen was determined by sodium sulfite precipitation (Rampling, M. W., et al., *Clin. Chim. Acta* 67:43–52 (1976)).

$\alpha_2$-Antiplasmin and Plasminogen Assays $\alpha_2$-Antiplasmin (Edy, J., et al., Thromb. Res. 8:513–518 (1976)) and plasminogen (Friberger, P., et al., In *Chromogenic Peptide Substrates*, Skully, M. F., et al., (eds.), pp. 128–140, Churchill Livingstone, Edinburgh, Scotland (1979)) levels were measured as a percentage of normal levels in citrated human or rabbit plasma in the S-2251 chromogenic substrate assay.

HYBRIDOMA BISPECIFIC ANTIBODY F32.1

Preparation of Fibrin-Like α Peptide

An oligopeptide corresponding to the amino terminus of the a chain of fibrin was assembled by solid-phase peptide synthesis on a methylbenzhydrylamine HCl resin. The dodecapeptide Gly-Pro-Arg-Val-Val-Glu-Arg-His-Gln-Ser-Ala-Cys (α peptide) was cleaved with HF and hydrolyzed and the amino acid composition was determined. The peptide was also analyzed by high performance liquid chromatography. α Peptide was coupled to keyhole limpet hemocyanin with bromoacetyl N-hydroxy succinimide. The degree of peptide substitution on the keyhole limpet hemocyanin was determined by amino acid analysis for carboxymethylated cysteine.

BALB/c mice were immunized with 50 μg of α peptide linked to keyhole limpet hemocyanin in complete Freund's adjuvant and boosted one month later with 25 μg of e peptide in incomplete Freund's adjuvant. Before the mice were killed, the presence of anti-α peptide antibodies in serum was verified by RIA (as described below). Then HGPRT[31] TCL8 hybridoma cells were fused with spleen cells harvested from mice that had been immunized with α peptide, at a ratio of 10 splenocytes per hybridoma cell. Cells were applied to 96-well microtiter plates at 10 and 5 spleen cells per well and were incubated for 5 in conditioned medium (containing 100 μl of culture supernatant from normal mouse spleen cells that had been previously cultured for 4 days). After 5 days, 100 μl of supernatant was removed and replaced with fresh HAT medium. When cell growth was visible macroscopically, 50 μl of supernatant was removed for RIA, which tested for antifibrin and anti-tPA activities. When both activities were detected in a single well, the fusion products were placed into 24-well plates and subsequently subcloned three times at limiting dilution (0.5 cells per well).

Other Assays

For purification, an e peptide-Sepharose column was prepared as described for the β peptide-Sepharose column. Bispecific antibody F32.1 was purified with e peptide- and tPA-Sepharose columns by the methods described for F36.23. Isotyping, radioimmunoassay to assess dual specificity, and characterization of F32.1 and F32.1 F(ab')$_2$ were also performed as for F36.23, with the exception that for F32.1 α peptide-Sepharose was substituted for β peptide-Sepharose. Also, for F32.1 in vitro fibrinolysis was assayed with antibody at 0.53 mg/ml, and with serial dilutions. The maximal enhancement of lysis was observed at 6.6 μg/100 μl.

Results

Preparation and Purification of Bispecific Antibodies

Antifibrin antibody 59DB hybridoma cells and anti-tPA antibody TCL8 cells were drug-marked as described. To assure that TK 59D8 cell supernatants did not cross-react with tPA and that HGPRT TCL8 cell supernatants did not cross-react with fibrin, each was screened in solid-phase assays for tPA or fibrin monomer binding, respectively. Supernatants from both cell lines reacted with the appropriate substrates and did not demonstrate cross-reactivity (data not shown). In addition, when culture supernatant from HGPRT TCL8 was chromatographed on α peptide- or β peptide-Sepharose, neither the fall through nor nonspecifically bound eluate reacted with fibrin. Analogously treated culture supernatant from TK$^-$ 59DB also failed to react with tPA (data not shown).

Figure 9A:
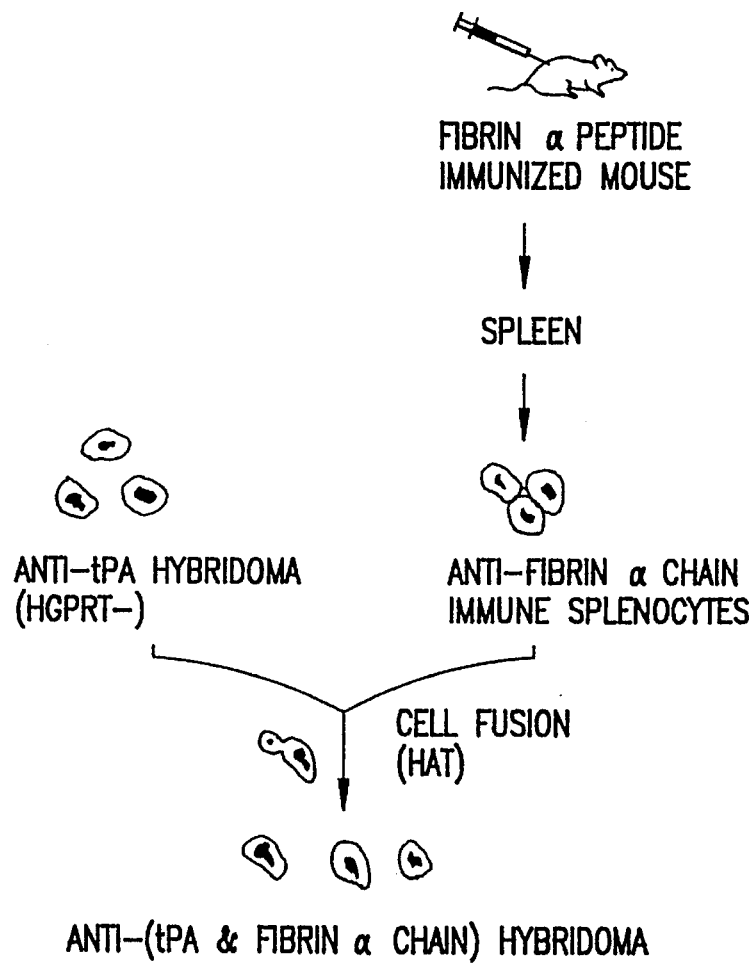
FIGS. 9A and 9B. Generation of bispecific antibodies. Panel A illustrates the production of the F32.1 hybridoma by fusion of immune splenocytes and HGPRT_ TCL8. Panel B illustrates the production of the F36.23 hybrid hybridoma by fusion of HGPRT_ TCL8 with TK_ 59D8.
Figure 9B:
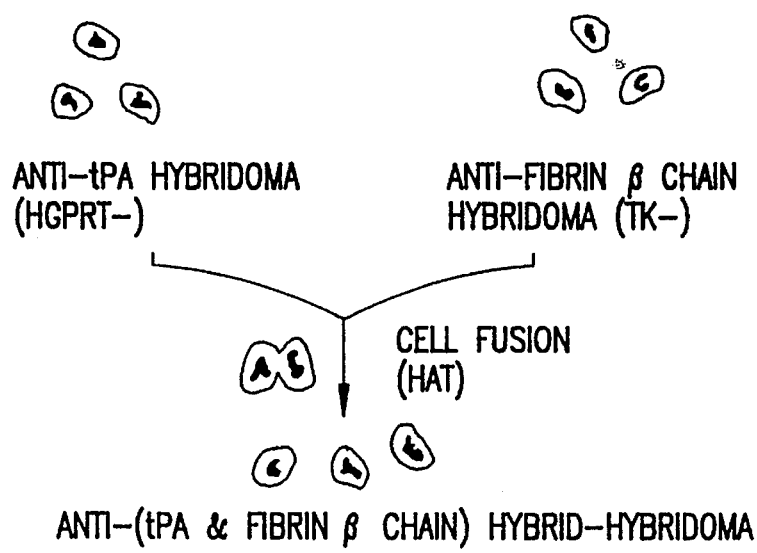

These cell lines were then fused to produce hybridhybridoma bispecific antibody F36.23. Our primary intention was to generate a bispecific antibody whose parent antibodies were well characterized. However, one could also envision combining a well-characterized antibody with a newly generated antibody. To test the validity of this strategy, we fused HGPRT$^-$ TCL8 cells with splenocytes from a mouse that had been immunized with an oligopeptide representing the amino-terminal sequence of the a chain of fibrin, thereby producing hybridoma bispecific antibody F32.1. FIG. 9 summarizes the two strategies.

Four weeks after the fusion of the 59D8 and TCL8 hybridoma lines, 29 of 768 wells contained surviving cells. Supernatants from the 29 wells were assayed by RIA. Antifibrin and anti-tPA activities were evident in 4 of the 29 wells. After three subcloning steps at limiting dilution, a single, stable, monoclonal cell line (F36.23) was identified.

Two weeks after the fusion of the fibrin α peptide-immune splenocytes with TCL8, colonies were viable in 18 of 170 wells. Supernatants from the 18 wells were assayed by RIA. One well showed both antifibrin and anti-tPA activities. The cells were expanded and subcloned at limiting dilution three times to yield a stable monoclonal line (F32.1).

Figure 10:
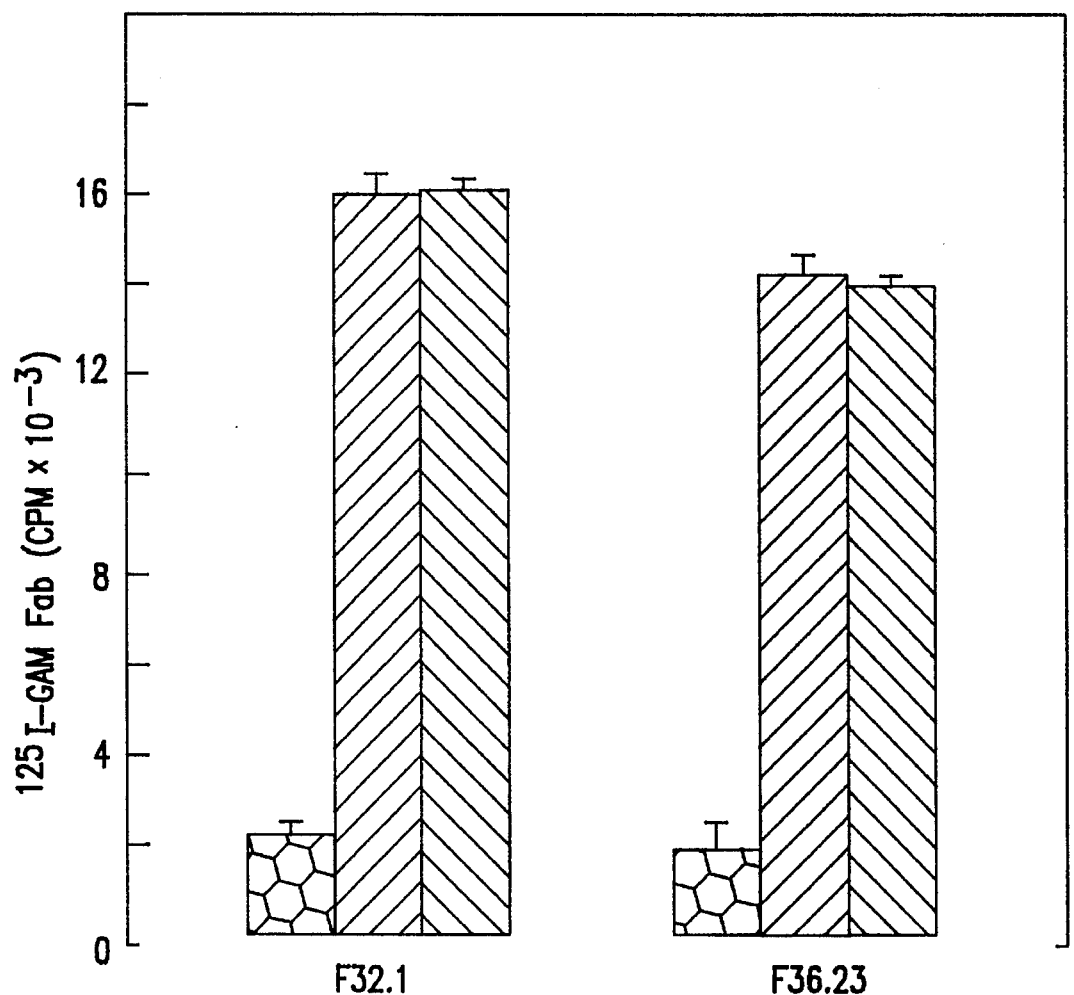
FIG. 10. Dual antigen-binding ability of bispecific antibodies F32.1 and F36.23 by solid phase RIA. The stippled bar in each group represents background binding, the lightly cross-hatched bar binding to tPA, and the heavily cross-hatched bar binding to fibrin monomer. The means of triplicate determinations from a representative experiment are shown; error bars indicate standard deviations.

Both F36.23 and F32.1 cell lines were then amplified in CAF/J mouse ascites. Because ascites would be expected to contain various antibody recombinant forms, bispecific monoclonal antibodies were isolated by affinity purification from their bivalent monospecific parental antibodies, from monovalent antibodies, and from nonfunctional H-L chain associations. After the F36.23 and F32.1 bispecific antibodies had been chromatographed against the appropriate fibrin-like peptide and tPA immunoabsorbent resins, the antibodies were tested for the ability to bind both tPA and fibrin monomer in solid-phase assays (FIG. 10). Thus "dual specificity" was confirmed.

Characterization of Bispecific Antibody F36.23

The isotype of parental cell lines 59D8 and TCL8 (and of the corresponding drug marked lines) was $IgG_1\kappa$. The isotype of F36.23 was, as expected, $IgG_1\kappa$. To further verify that the results of the functional studies and the fibrin and tPA-specificity studies were due to both specificities residing on a single antibody molecule, the N-terminal amino acids of 59D8, TCL8, and F36.23 were sequenced. Degradation of TCL8 revealed a single sequence consistent with L chain, suggesting the presence of a blocked H chain. Studies of F36.23 revealed sequences consistent with 1 H and 2 L chains, at equimolar ratios. At the third residue, Leu (TCL8 L chain), Val (59D8 L chain), and Glu (59D8 H chain) were present in equimolar quantities, confirming the H1L1-H2L2 stoichiometry (data not shown).

Determining the Percentage of Bispecific Antibody in Ascites Affinity Chromatography To determine the binding efficiency of affinity chromatography, purified antibodies 59DB and TCL8 were chromatographed on 9 peptide-Sepharose and tPA-Sepharose columns, respectively: 91% of purified 59DB was eluted from the β peptide column and 88% of purified TCL8 was eluted from the tPA column. For F36.23 ascites (4.4 mg of IgG/ml), 41% bound to the β peptide-Sepharose column and, of the eluted fraction, 56% bound to the tPA-Sepharose column. Thus, 23% of F36.23 gamma globulin was recovered as bispecific antibody. For F32.1 ascites, no corresponding purified antibody was available for affinity chromatography because the anti-α peptide portion of the antibody was derived from immunized spleen cells directly. F32.1 ascites (4.7 mg of IgG/ml) was first chromatographed on the α peptide-Sepharose column: 26% of the total IgG bound. Of the eluted fraction, 20% bound to the tPA-Sepharose column. Thus, 5% of the total IgG in F32.1 ascites was bispecific.

Simultaneous Binding of Two Antigens the Bispecific Antibodies

Even though a bispecific antibody can bind two antigens, it is conceivable that it would be unable to bind the two antigens simultaneously. This possibility was tested as follows. tPA or fibrin monomer was applied to 96-well plates, and, after incubation with double-affinity purified bispecific antibody (0.05 mg/ml), a $^{125}$I-labeled probe (D2E or tPA, respectively) was used to detect the ability to simultaneously bind both fibrin and tPA (FIG. 11). These assays demonstrated that bivalency occurs in the purified F36.23 and F32.1 bispecific antibody molecules.

Fibrinolysis with Bispecific Antibodies

Figure 12:
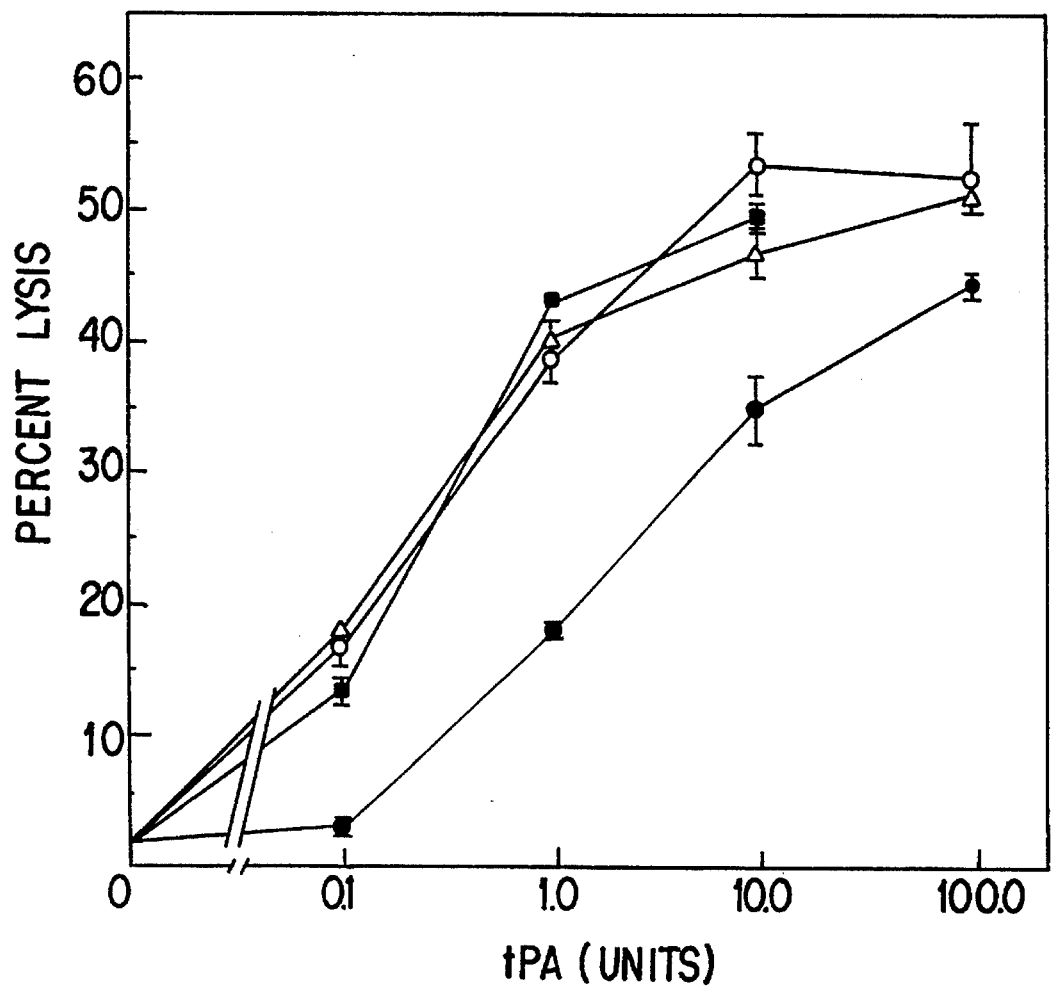
FIG. 12. In vitro fibrinolysis by tPA, by tPA and F36.23, and by the F36.23-tPA immunoconjugate. Filled circles show fibrinolysis by tPA alone, triangles show fibrinolysis by tPA with F36.23 added separately, open circles show fibrinolysis by tPA-F36.23 immunoconjugate purified by elution from a benzamidine-Sepharose resin, and squares show fibrinolysis by tPA-F36.23 immunoconjugate purified by elution from a β peptide-Sepharose column. Each point represents the mean of triplicate determinations from a single experiment, and error bars show standard deviations.

After having determined that both anti-tPA and antifibrin specificities resided on individual bispecific antibody molecules, we investigated the possibility of using them to specifically target tPA. FIG. 12 shows the results of a representative fibrin monomer-Sepharose assay in which the potency of tPA was measured alone, in the presence of F36.23 bispecific antibody, and as part of an F36.23-tPA immunoconjugate. When the F36.23 and tPA were added separately to the assay system, the fibrinolytic potency of tPA was enhanced 14.6 fold (P<0.0001). When F36.23 and tPA were introduced into the assay as an immunoconjugate, in an attempt to more closely represent physiologic conditions, F36.23-tPA purified by chromatography on Sepharose-immobilized benzamidine or Sepharose-immobilized β peptide was 22.7- and 22.4-fold more potent, respectively, than an equal amount of tPA alone (P<0.0001, FIG. 2). Evaluation of the F32.1 bispecific antibody demonstrated similar effects (data not shown).

Fibrinolysis with Bispecific F(ab')$_2$

Figure 13:
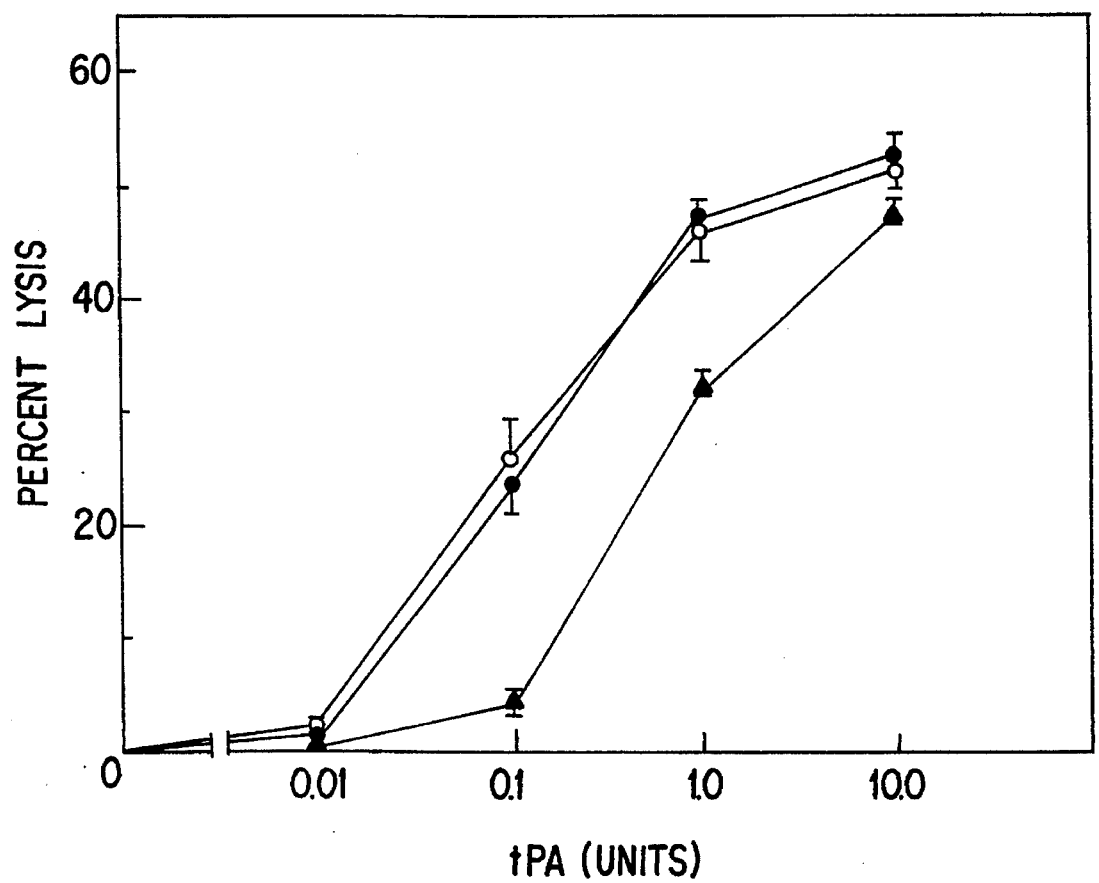
FIG. 13. In vitro fibrinolysis by tPA in the presence of bispecific F36.23 and F32.1 F(ab')$_2$ fragments. Open circles show fibrinolysis with tPA and F32.1 F(ab')$_2$, filled circles show fibrinolysis with F36.23 F(ab')$_2$, and filled triangles show fibrinolysis by tPA alone. Each point represents the mean of triplicate determinations from a single experiment, and error bars show standard deviations.

Because of their size and lack of $F_c$ domain, F(ab')$_2$ fragments would be better suited for clinical use. FIG. 13 shows the results of a representative experiment in which we studied the relative fibrinolytic potency of tPA in the presence of bispecific antibodies as F(ab')$_2$. F36.23 F(ab')$_2$ and F32.1 F(ab')$_2$ produced 4.8- and 5.2-fold enhancements, respectively, in the potency of tPA.

Thrombolysis in vivo

Finally, we tested the ability of bispecific antibody F36.23 to increase the fibrinolytic potency of tPA in the rabbit jugular vein model. We infused tPA alone (over a range of concentrations), F36.23 (2.2 mg/kg) and tPA, or anti-tPA antibody TCL8 (2.2 mg/kg) and tPA. The infusion of TCL8 followed by tPA served to determine whether the thrombolytic potency of tPA was affected by binding to an antibody that has the known effect of prolonging the plasma half-life of tPA (and perhaps other unknown effects) but does not contribute fibrin specificity. When tPA was administered with antibody F36.23, the thrombolytic potency of tPA increased overall by 1.6 fold (P<0.01). The co-administration of TCL8 and tPA produced a decrease in the potency of tPA that did not attain statistical significance (P=0.1); however, the decrease does suggest that TCL8 has some inhibitory effect on tPA. Other studies have shown that TCL8 inhibits the catalytic activity of tPA by a factor of 2 (Dr. Mary E. Russell, personal communication). Fibrinogen and anti-plasmin levels did not significantly decrease at any of the dosages tested (data not shown).

Discussion

It has been shown that bispecific monoclonal antibodies retain dual native binding specificity (Milstein, C., et al., *Nature* (London) 305:537–40 (1983)). The capacity to recognize two antigens has been used to focus human T cells to tumor cells (Staerz, D., et al., *Proc. Natl. Acad. Sci. USA* 83:1453–57 (1986)) or to cells bearing various surface antigens (Lanzavecchia, A., et al., *Eur. J. Immunol.* 17:105–11 (1987)). We sought to use the same strategy for targeting an enzyme, tPA, to its effector site on human fibrin by means of a fibrin specific monoclonal antibody. We produced two bispecific antibodies, a hybridoma (F32.1) and a hybrid-hybridoma (F36.23), each possessing tPA and fibrin specificity. Although for our purposes it was necessary to have two different, well characterized antibodies, we also suggest that it might be desirable to be able to generate bispecific antibodies for which one antibody binding site is well characterized and the other binding site represents a new epitope. For this reason we developed the two schemes for hispecific antibody generation shown in FIG. 9.

To increase the likelihood of random heavy chain association in developing bispecific antibodies, we chose for hybridization parental antibodies of the same isotype (IgGl, κ). Sequencing studies were undertaken to further characterize the bispecific antibodies and to confirm that the antifibrin (59D8) and anti-tPA (TCL8) specificities resided on a single antibody molecule. Although the H chain of TCL8 was blocked to Edman degradation, N-terminal amino acid sequencing of F36.23 verified the presence of 59DB H, 59DB L, and TCL8 L chains in the double affinity-purified antibody. Additionally, the ratios of the chains obtained by N-terminal amino acid sequencing suggested that one of each of the expected chains—59D8 H, 59DB L, TCL8 H, and TCL8 L—was present in the hybrid molecule.

In the association of H and L chains by a hybridoma, 10 molecular species are expected (Milstein, C., et al., *Nature* (London) 305:537–40 (1983)). By determining the relative quantities of bispecific and monospecific antibodies, we were able to postulate two different patterns of hybridoma chain recombination in F32.1 and F36.23. For F32.1, the 5% yield of bispecific antibody suggested that random association of H and L chains had occurred, so that each of the 10 molecular species was produced in approximately equimolar ratios. For F36.23, however, the 23% yield of bispecific antibody was more suggestive of fully restricted L chain association and random H chain association. The pattern of chain recombination for F36.23 would be expected to produce the highest frequency of bispecific antibodies (Suresh, M., et al., *Meth. Enzymol.* 121:210–28 (1986)).

The bispecific antibodies purified according to these methods retained antifibrin and anti-tPA specificities (FIG. 10). Additionally, when the affinity-purified bispecific antibodies were tested for dual specificity in an RIA in which one antigen was adsorbed to the plate while the other antigen was used as probe, both bispecific antibodies bound to the second antigen, whereas the two monospecific parental antibodies did not.

Figure 11A:
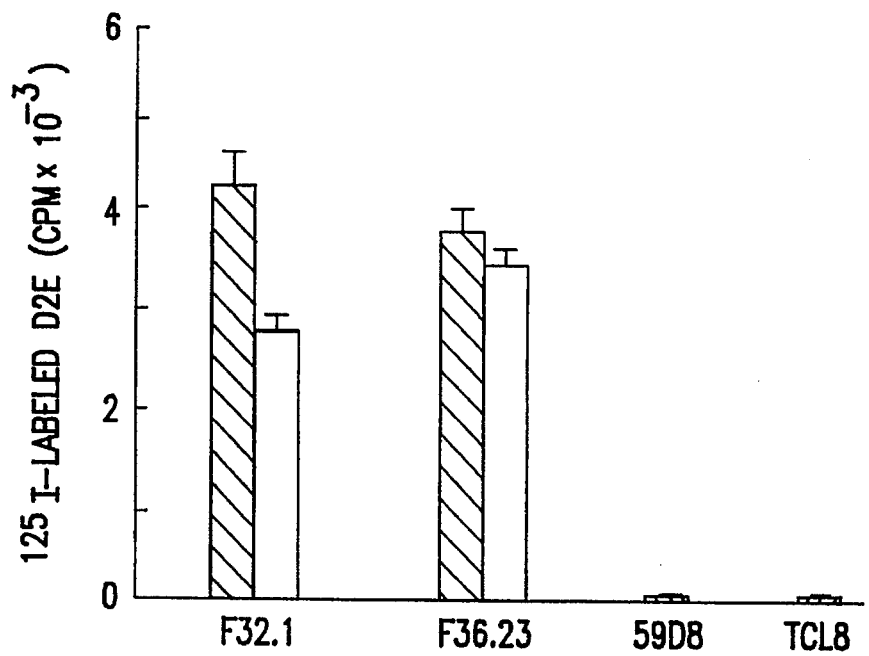
FIGS. 11A and 11B. Demonstration of simultaneous binding of bispecific antibodies and their F(ab')$_2$ fragments to fibrin and tPA. Striped bars represent binding by intact antibodies and stippled bars represent binding by F(ab')$_2$ fragments. The means of triplicate determinations from a representative experiment are shown; error bars indicate standard deviations. Nonspecific antibody adherence to the wells was no greater than 180 cpm for any sample. The upper panel shows the results of a representative experiment in which tPA was used as fixed antigen and $^{125}$-labeled D2E, a fibrin fragment bearing both the A and B epitopes, was used as probe. The lower panel shows the results of a representative assay in which fibrin was used as fixed antigen and $^{125}$I-labeled tPA was used as probe.
Figure 11B:
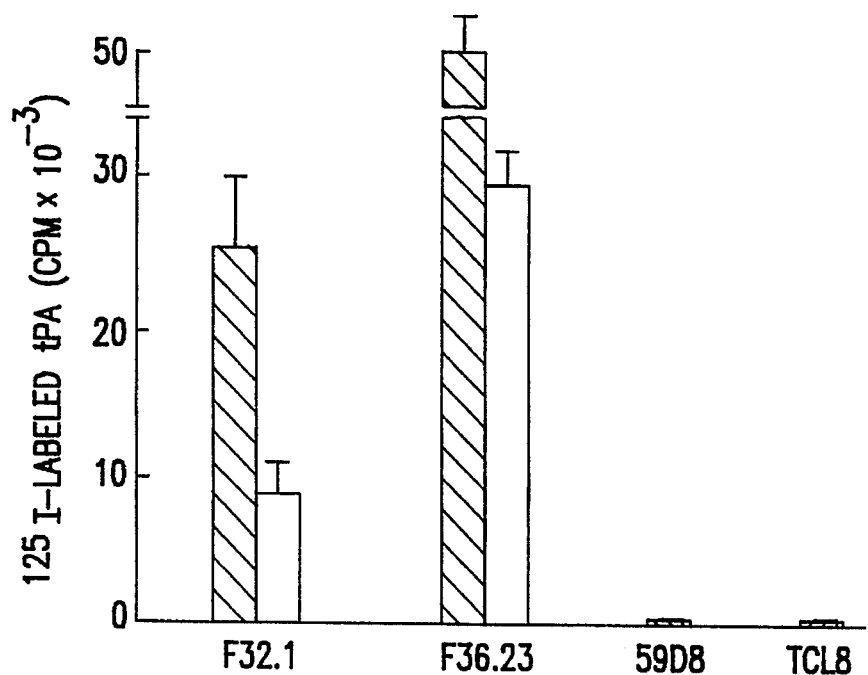

F(ab')$_2$ fragments bearing antifibrin and anti-tPA specificities might be less immunogenic because they are smaller (with shorter plasma half-lives) and lack the F$_c$ fragment, which is highly immunogenic. In addition, by using F(ab')$_2$ fragments instead of whole bispecific antibodies, it may be possible to approximate the two antigens and thereby to identify steric influences that could not be detected with our previous constructs. As shown in FIGS. 11A and 11B, the F36.23 and F32.1 bispecific F(ab')$_2$ fragments retained the ability to bind two antigens.

The ability of bispecific antibody F36.23 to bind both antigens when fixed to fibrin on a solid matrix, and the ability of tPA to activate plasminogen when bound to the antibody, was studied in an in vitro model of fibrinolysis (FIG. 12). We postulate that F36.23 augments fibrinolytic activity while bound to fibrin by binding tPA at the anti-tPA F$_{ab}$ region. This dual binding may result in plasminogen activation at the fibrin site and thus in a higher concentration of plasmin available for fibrinolysis. When bispecific F36.23 and F32.1 F(ab')$_2$ fragments were tested in the in vitro model (FIG. 13), they both resulted in a similar enhancement of tPA activity.

Studies of tPA as part of an immunoconjugate with F36.23 (FIG. 12) showed that binding of bispecific antibody to tPA before contact with fibrin, as might occur in human plasma, did not alter the antibody's ability to target the enzyme or to enhance its potency in vitro. When tested in vivo, bispecific antibody F36.23 increased the thrombolytic potency of tPA 1.6 fold. Evidence that anti-tPA antibody TCL8 partly inhibits tPA in this assay may explain why F36.23 did not produce a more pronounced effect in vivo. Given the ability of 59DB to target tPA when it is present at nanogram concentrations, it is plausible to imagine using bispecific antibodies to concentrate endogenous tPA at the site of a thrombus. Thus bispecific antibodies could obviate the need to administer exogenous tPA. Also, because the use of bispecific antibodies would avoid fibrinogenolysis, it holds promise for decreasing the hemorrhagic complications of thrombolytic therapy.

Example 9

The following example describes the preparation and biochemical characterization of a bispecific (antifibrin-antiurokinase) antibody. A high-affinity antifibrin monoclonal antibody, 59D8, was chemically coupled to an antiurokinase monoclonal antibody, PEG2. PEG2 was produced by fusing SP2/0 cells with spleen cells from mice immunized with human high molecular weight two-chain urokinase.

MATERIALS AND METHODS

High molecular weight two-chain urokinase (100,000 IU/mg) was purchased from Serono Laboratories; Tris(hydroxymethyl)aminomethane from Aldrich; fibrinogen from Kabi Vitrum; $^{125}$I-labeled fibrinogen (IBRIN) from Amersham; IODO-GEN, 2-iminothiolane HCl, and N-succinimidyl-3-(2-pyridyldithio)propionate (SPDP) from Pierce Chemical; iodoacetamide from Sigma; DE52 from Whatman; and Sephacryl ALA34, Sephacryl 5-300, and Sepharose CL4B from Pharmacia Fine Chemicals. The high molecular weight scuPA was a generous gift of Dr. Desire Collen, University of Leuven, Belgium.

Antibody Production

Monoclonal antibody 59DB, which is specific for an epitope at the amino terminus of the β chain of fibrin, was raised and purified as previously described (Hui, K. Y., et al., *Science* 222:1129–1132 (1983)). Urokinase-specific monoclonal antibody PEG2 was produced as follows. Female A/J mice were immunized with 25 μg/mouse urokinase (human high molecular weight two-chain urokinase unless otherwise specified) in complete Freund's adjuvant and were rechallenged four weeks later with urokinase (25 μg/mouse) in incomplete Freund's adjuvant. Somatic cell fusion was performed according to the method of Köhler and Milstein (Köhler, G., et al., *Nature* (London) 256:495–497 (1975)) as modified by Galfre et al., (Galfre, G., et al., *Nature* (London) 266:550–552 (1977)). A solid-phase radioimmunoassay identified twelve clones positive for urokinase. PEG2 was selected for expansion and purification because of its high-affinity binding to both scuPA (high molecular weight unless otherwise specified) and urokinase.

Antibody Expansion and Purification

Ascites containing PEG2 were produced in pristane-primed A/J mice. Antibodies were purified by DEAF-cellulose ion exchange chromatography (DE52). Ascites containing 59D8 were produced in pristane-primed BALB/C retired breeder mice. Antibody 59D8 was further purified by affinity chromatography on a column of Sepharose linked to the peptide against which it had been raised Gly-His-Arg-Pro-Leu-Asp-Lys Cys: peptide Bβ(15-21) plus Cys (Hui, K. Y., et al., *Science* 222:1129–1132 (1983)).

Conjugation of Antifibrin Antibody to Antiurokinase Antibody

SPDP-modified 59D8 was conjugated to 2-iminothiolane-modified PEG2 by disulfide bond formation, according to the method of Liu et al. (Liu, M. A., et al., *Proc. Natl. Acad. Sci. USA* 82:8648–8652 (1985)) with the following modifications. Purified PEG2 (15 mg) was dialyzed against 0.14M sodium chloride, 1 mM potassium chloride, and 3.7 mM sodium phosphate, pH 7.4 (conjugation buffer) and then reacted with a 200-fold molar excess of 2-iminothiolane HCl dissolved in 25 mM sodium borate, pH 9.1, for 30 min. At the end of the incubation the modified PEG2 was dialyzed into phosphate-buffered saline azide (PBSA), pH 6.6.

Affinity-purified 59D8 (15 mg) was dialyzed against conjugation buffer and incubated with a 10-fold molar excess of SPDP dissolved in ethyl alcohol for 30 min. At the end of the incubation the modified 59D8 was dialyzed into conjugation buffer overnight.

2-Iminothiolane-modified PEG2 was mixed with SPDP-modified 59D8 in an equimolar ratio and incubated overnight at 4° C. The reaction was terminated by the addition of a 100-fold molar excess of iodoacetamide. The reaction mixture was then fractionated by gel filtration on a Sephacryl S-300 column (2.5×60 cm) and equilibrated with PBSA and 1M urea, pH 6.6. Fractions were collected and aliquots of those absorbing at 280 nm were subjected to sodium dodecyl sulfatepolyacrylamide gel electrophoresis (SDS-PAGE) and radioimmunoassay.

Characterization of Bispecific Antibody

Dual Antigen-binding Radioimmunoassay. Microtiter plates were coated with 25 μL of either fibrin monomer (10 μg/mL) or scuPA (10 μg/mL), blocked with 10% horse serum, and washed ten times with deionized water to remove nonspecifically bound ligand. Culture supernatant containing 59D8, PEG2, or samples of fractions presumed to contain bispecific antibody were plated in duplicate wells and allowed to react for 1 h. After the plates had been washed ten times with water, 25 μL of either $^{125}$I-labeled goat anti-mouse Fab' (approximately 50,000 cpm/25 μL) or $^{125}$I-labeled scuPA (approximately 50,000 cpm/25 μL) was placed in the wells. Control wells contained no radiolabeled probe. After a 1-h incubation, excess probe was washed from the plates with water and the wells were measured for specifically bound radioactivity in a gamma counter.

Fibrin-Sepharose Assay. Fibrin monomer-Sepharose was prepared by coupling $^{125}$I-labeled fibrinogen (IBRIN) to cyanogen bromide-activated Sepharose CL4B. The immobilized fibrinogen was converted to fibrin by the addition of human thrombin in the presence of 100 mM $CaCl_2$ (Bode, C., et al., *Science* 229:765–767 (1985)). The assay was conducted as follows. $^{125}$I-labeled fibrin-Sepharose (100 μL) containing 60,000 cpm/100 μL was pipetted into 5-mL Sarstedt tubes. A solution (100 μL) of scuPA (yielding final concentrations of $1.852 \times 10^2$ pM, $1.852 \times 10^1$ pM, $1.852 \times 10^0$ pM, $1.852 \times 10^{-1}$ pM, $1.852 \times 10^{-2}$ pM, or $1.852 \times 10^{-3}$ pM) and either 100 μL of bispecific antibody (0.01 mg/mL) in PBSA or 100 μL of PBSA alone was added to the test tubes and allowed to incubate for 3 h. After an initial washing step with 0.1M Tris-HCl, 0.1M sodium chloride, 0.1% Tween-80, 0.5% Triton X-100, and 0.5% bovine serum albumin, pH 7.4 (3 mL/tube), the tubes were washed three times with Tris-buffered saline azide (TBSA), pH 7.4. At the end of each washing step the tubes were spun in a centrifuge for 5 min at 2000 rpm and supernatant was carefully removed. After the last wash all but 100 μL of the supernatant was removed. Lysine-Sepharose-purified plasminogen (1 mL/tube of 0.15 mg/mL plasminogen) was then added to each sample and incubated at room temperature overnight. The tubes were counted in the gamma counter and 600 of supernatant (50% of total volume) was pipetted out of each, transferred to a second tube, and counted in the gamma counter. Percent lysis for each sample was calculated as (supernatant counts×200) total counts.

Plasma Clot Assay. The in vitro plasma clot assay was performed essentially as described by Lijnen et al. (Lijnen, H. R., et al., *Thromb. Haemostas.* 52:31–33 (1984)). To thawed fresh-frozen human plasma (FFP) was added $^{125}$I-labeled human fibrinogen (IBRIN; 100,000 cpm/mL FFP), calcium chloride (to 50 mM), and 8 NIH units of thrombin/mL FFP. This mixture was drawn into Silastic tubing (inner diameter 4 mm) and incubated at 37° C. for 30 min. One-inch clot segments were cut from the tubing and the clots were extruded into 5-ml Sarstedt tubes. The clots were washed in saline and counted in a gamma counter before use. To each tube was added 2 mL of thawed FFP and a solution containing 100 μL of scuPA (yielding final concentrations of 3704 pM, 1852 pM, 926 pM, 463 pM, 185.2 pm, or 92.6 pM) with or without 100 μL of bispecific antibody. Every hour 750 μL of supernatant was removed from each tube, counted, and replaced. Percent lysis for each tube was calculated as (supernatant counts×300)+total counts. Samples were saved at the end of the experiment for determination of fibrinogen levels.

Fibrinogen Assay. The fibrinogen content of samples of citrated human plasma was determined by two methods: Clottable fibrinogen was measured by the method of Clauss et al. (Clauss, A., *Acta Haematol.* 17:237–246 (1957)) and precipitable fibrinogen content was determined by the sodium sulfite method (Rampling, M. W., et al., *Clin. Chim. Acta* 67:43–52 (1976)).

Quantitation of 59D8:PEG2 Ratio in Bispecific Antibody Preparations

PEG2 (100 μg) was radiolabeled with $^{131}$I and 59D8 (100 μg) with $^{125}$I by the IODO-GEN method (Fraker, P. J., et al., *Biochem. Biophys. Res. Commun.* 80:849–857 (1978)). The specific radioactivity of each iodination was calculated by the trichloroacetic acid protein precipitation method. Chemical conjugation of $^{131}$I-labeled PEG2 to $^{125}$I-labeled 59D8 was performed as described for the unlabeled species. The crude reaction mixture was then fractionated on a calibrated ACA-34 gel filtration column for purification. The protein content of each fraction was measured by absorbance at 280 nm, and the amount of $^{131}$I and $^{125}$I radioactivity in the peak protein fractions was simultaneously measured by dual-label gamma counting. The samples were also subjected to SDS-PAGE on 7.5% and 5% gels, followed by autoradiography.

RESULTS

Monoclonal antibody PEG2 was selected from a panel of twelve antibodies to urokinase on the basis of three criteria: PEG2 binds to both urokinase and scuPA, it does not inhibit the enzymatic activity of urokinase in an amidolytic or fibrin-plate assay, and its serotype is identical to that of 59D8 (IgGl-κ).

Figure 14:
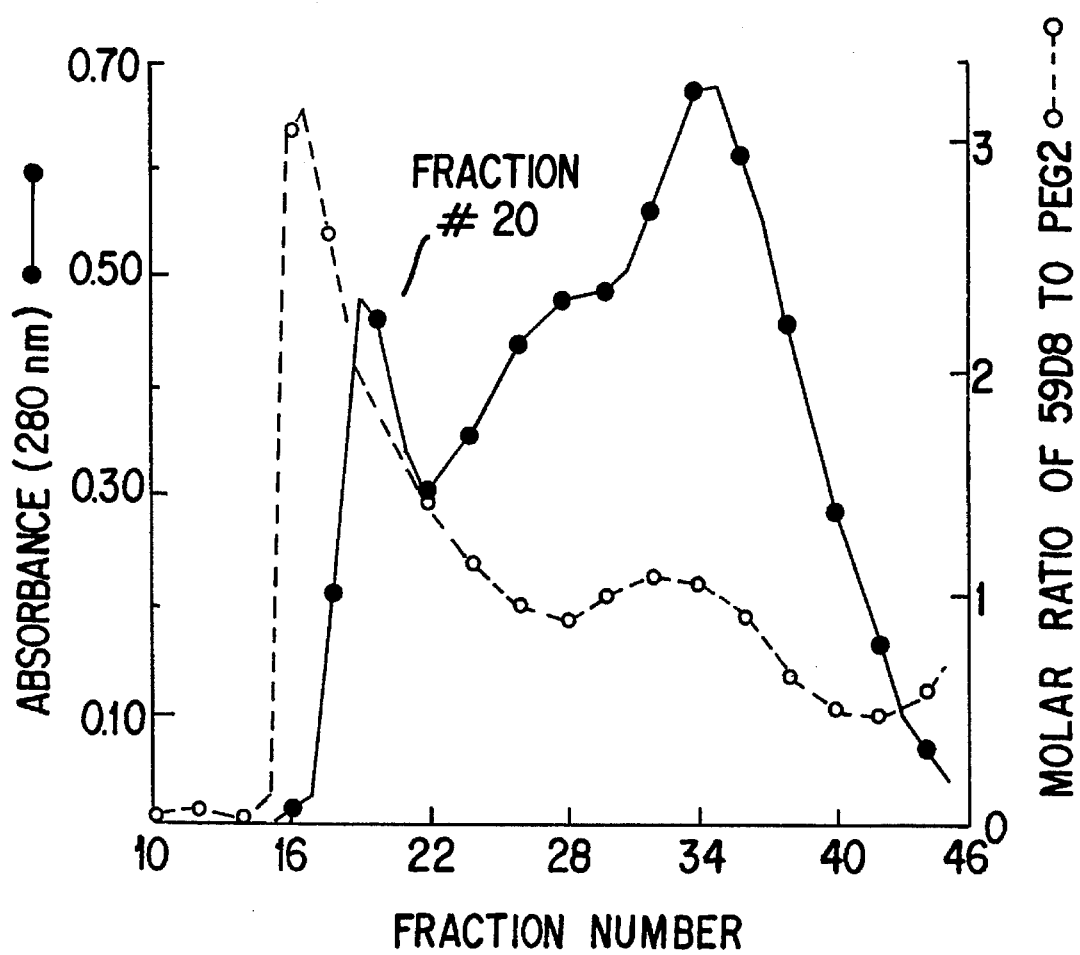
FIG. 14. ACA-34 gel filtration of conjugate reaction mixture. The solid curve represents the absorbance at 280 nm that is proportional to the protein content in each fraction. In each column fraction the ratio of $^{125}$I to $^{131}$I was calculated. This number represents the mean ratio of antibody 59D8 to antibody PEG2 in each fraction, shown by the dashed curve.
Figure 15:
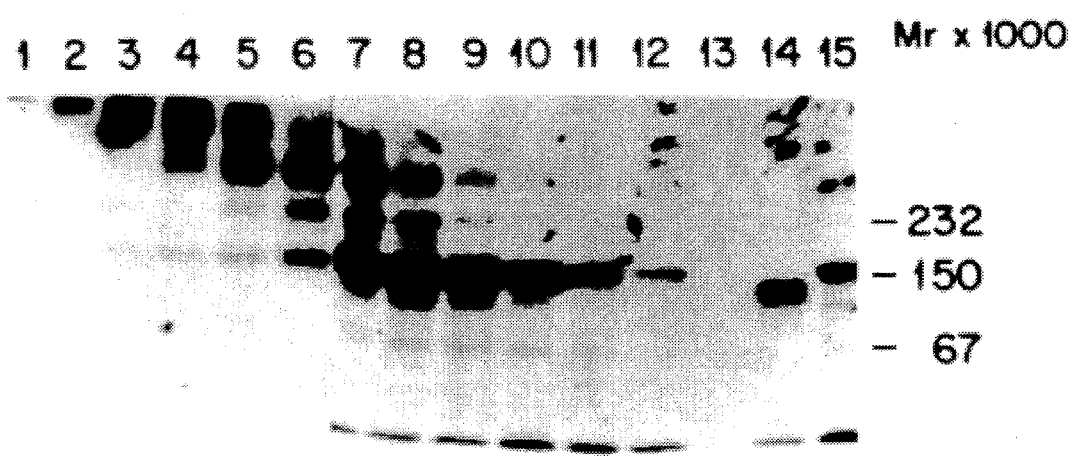
FIG. 15. Autoradiography of samples of crude bispecific antibody separated by gel filtration on an ACA-34 column. Aliquots of protein-containing fractions (from the gel filtration profile shown in FIG. 1) were subjected to SDS-PAGE on a 5% polyacrylamide gel. Lanes 1–12 contain aliquots of fractions 18, 20, 22, 24, 26, 28, 30, 32, 34, 36, 38, and 40, respectively. Lane 13 is blank. The 150,000-Dalton unconjugated constituent immunoglobulins, $^{131}$I-labeled PEG2 and $^{125}$I-labeled 59D8, are shown in lanes 14 and respectively.
Figure 16:
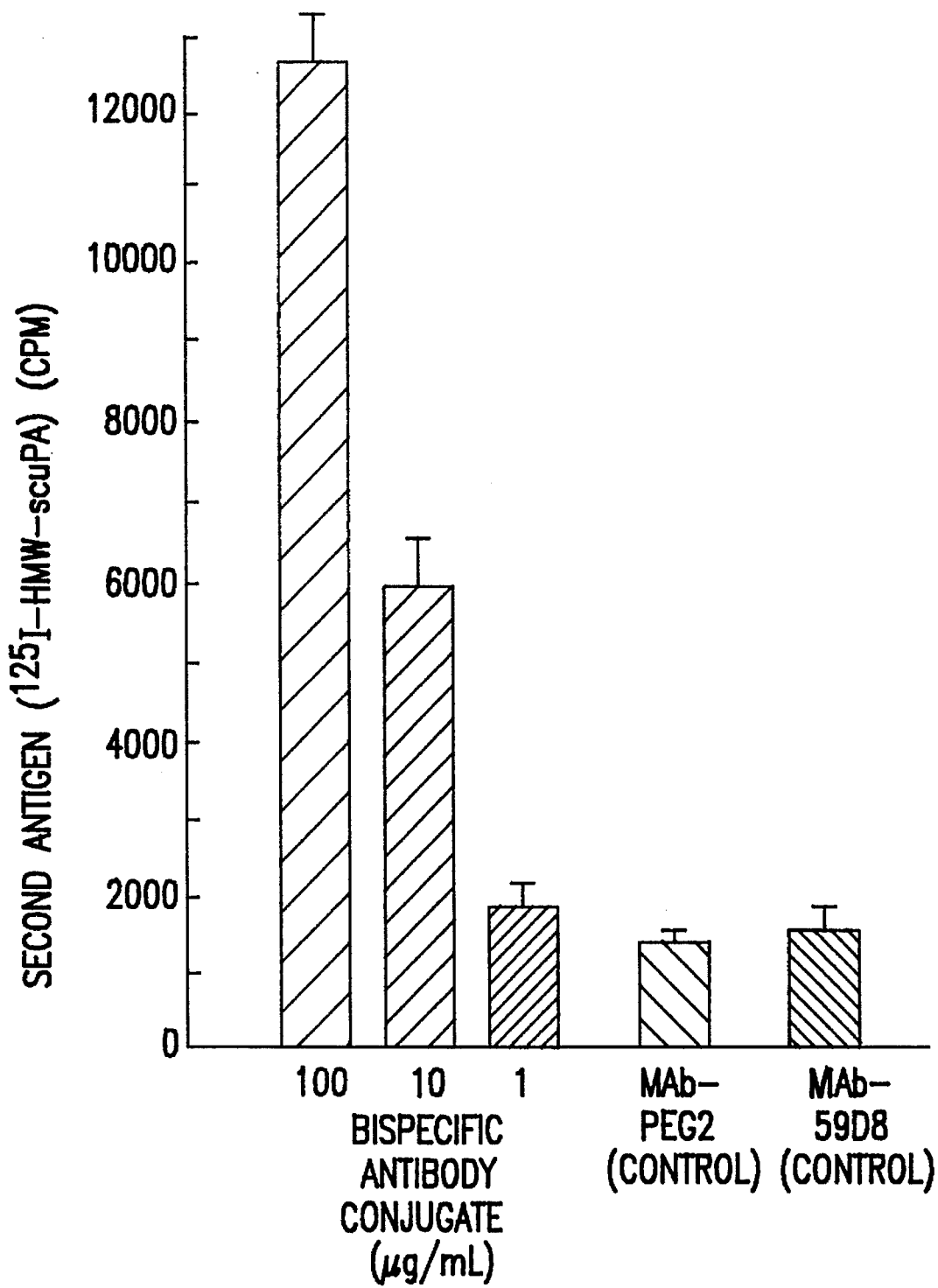
FIG. 16. Binding of bispecific antibody to fibrin monomer and scuPA. Microtiter plates were coated with fibrin monomer (10/µg/ml) and incubated with bispecific antibody (100 µ/ml, 10 µg/ml, 1 µg/ml), undiluted culture supernatant containing antiurokinase antibody PEG2, or undiluted culture supernatant containing antifibrin antibody 59D8. After the plates had been washed to remove excess and nonspecifically bound ligand, $^{125}$I-labeled scuPA was added to each well and allowed to incubate for one hour at 37° C. The bars represent the mean of three determinants±SEM (standard error of the FIG. 17. Effect of the bispecific antibody on fibrinolysis by scuPA in the fibrin-Sepharose assay. The enhancement of fibrinolysis by scuPA in the presence of the bispecific antibody (open circles) is shown with fibrinolysis by scuPA alone (filled circles). Each point represents the mean of three determinations±SEM.

After the conjugation of 59D8 to PEG2, the crude reaction mixture was size-fractionated by S-300 chromatography. The fraction eluting in the void volume contained aggregates of approximately 300,000 to 600,000 Daltons and greater (data not shown). The major peak within the column volume corresponded to approximately 150,000 Daltons. Radioimmunoassay demonstrated that 59D8 and PEG2 both retained their ability to bind antigen after chemical modification, and that the material in the void volume was capable of simultaneously binding both urokinase and fibrin monomer, while the included material was not (data not shown). The success of the chemical coupling strategy was assessed in experiments with bispecific antibody formed by conjugating 131I-labeled PEG2 to $^{125}$I-labeled 59D8 (FIGS. 14–16). The autoradiograph (FIG. 15) demonstrates the marked heterogeneity of conjugate species. Early fractions from the ACA-34 gel filtration column contained a single band with a molecular weight of approximately 600,000 Daltons probably representing tetramers of the constituent 150,000-Dalton imuunoglobulins 59D8 and PEG2. Late fractions contained protein bands probably representing tetramers, trimers, dimers, and unconjugated monomers. The included fractions showed primarily a single protein band at 150,000 Daltons that represents a mixture of unconjugated 59D8 and PEG2. These conclusions are supported by a graphic representation of the ratio of $^{125}$I to $^{131}$I in each column fraction (FIG. 14, dashed curve). Fractions 16–18 from the ACA-34 column contained bispecific antibody with a 59D8-to-PEG2 ratio of three to one. Therefore, the bispecific antibody contained in these fractions should consist of three 59D8 molecules bound to a single PEG2 antibody. Fractions 19–30 contained bispecific antibody in 59D8:PEG2 ratios of 2:1 and 1:1.

Several fractions from the ACA-34 column were tested for antigen binding to fibrin monomer and scuPA. FIG. 16 shows the results from an early fraction, 20, that contained bispecific antibody on the basis of its molecular weight by SDS-PAGE. The antigen-binding assay included the unconjugated immunoglobulins 59D8 and PEG2. Fraction 20 and 59D8 (but not PEG2) bound to fibrin monomer in a direct assay in which $^{125}$I-labeled goat anti-mouse Fab' was used as probe. Similarly, fraction 20 and PEG2 (but not 59D8) bound to scuPA ($^{125}$I-labeled goat anti-mouse Fab' probe). However, only fraction 20 simultaneously bound to fibrin monomer and $^{125}$I-labeled scuPA.

Figure 17:
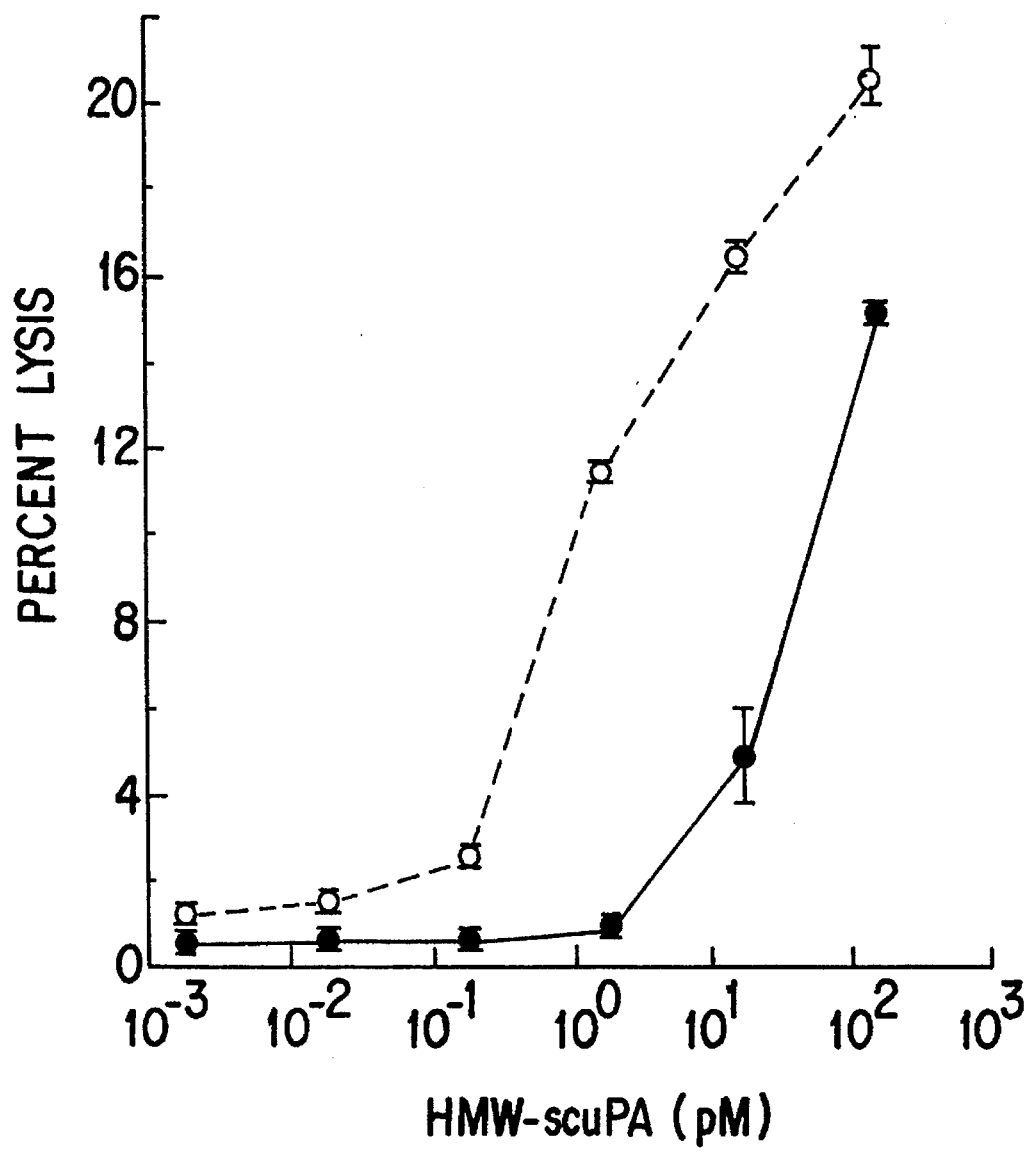
Figure 18:
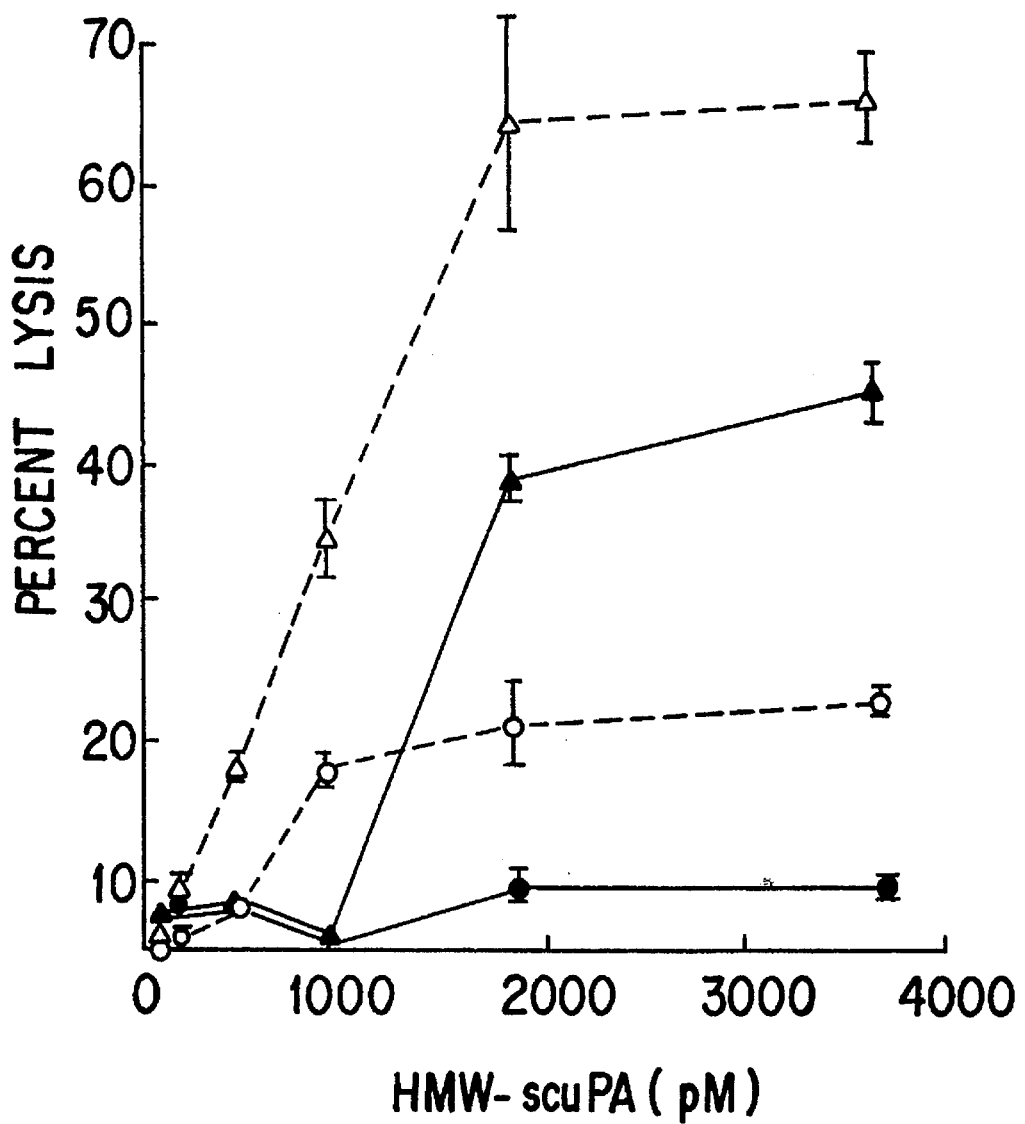
FIG. 18. Effect of bispecific antibody on human plasma clot lysis by scuPA. The enhancement of human plasma clot lysis by scuPA in the presence of the bispecific antibody (dashed lines, open symbols) is plotted against the effect of scuPA alone (solid lines, filled symbols) at one (circles) and two (triangles) hours. Each point represents the mean of three determinations±SEM.

Throughout the range of scuPA concentrations tested in the fibrin-Sepharose assay, lysis by scuPA in the presence of the bispecific antibody was greater than lysis by scuPA alone. For example, in samples containing the bispecific antibody, the fibrinolysis observed at a scuPA concentration of 1.85 μM was 12.8-fold higher than in samples lacking the bispecific antibody (i.e., the dose of scuPA, in the presence of the bispecific antibody, could be decreased to less than 2% of the dose of scuPA alone to achieve the same degree of fibrinolysis (FIG. 17)). The bispecific antibody also increased the lytic efficacy of scuPA in the human plasma clot assay at scuPA concentrations above 463 pM. At a scuPA concentration of 463 pM, plasma clot lysis by scuPA in the presence of bispecific antibody (measured as the release of iodinated fibrin degradation products into the plasma supernatant) increased by 5.6 fold relative to that for scuPA alone at two hours' incubation (FIG. 18).

Figure 19:
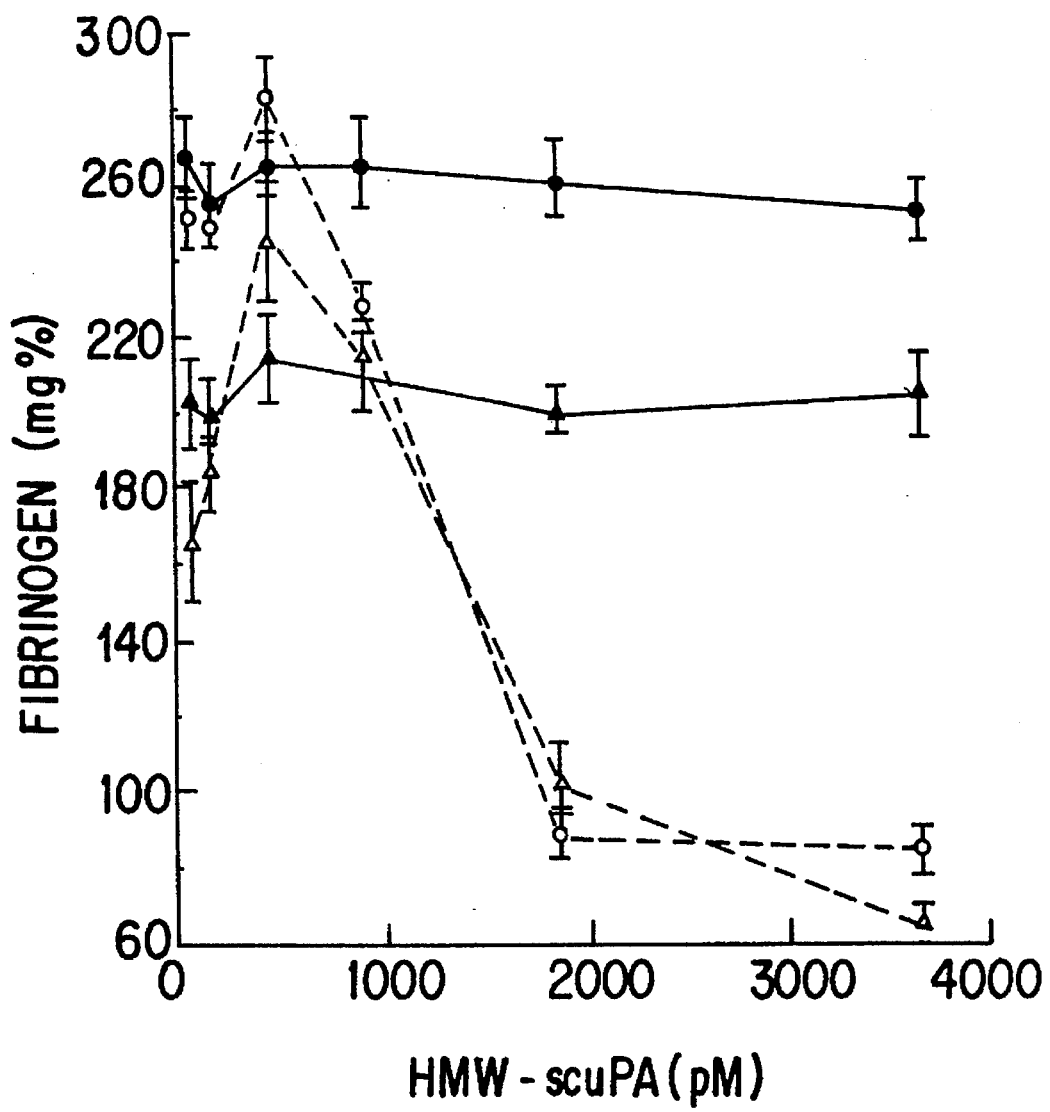
FIG. 19. Effect of bispecific antibody on residual fibrinogen concentration in the human plasma clot assay. Fibrinogen levels were measured by the Clauss (circles) and precipitable fibrinogen (triangles) methods. Solid lines and filled symbols show residual fibrinogen levels in clots lysed in the presence of both scuPA and bispecific antibody. Dashed lines and open symbols show residual fibrinogen levels in clots lysed with scuPA alone. The points represent the means of two determinations±SEM.

The fibrinogen content of samples from the plasma clot assay was also determined. In samples containing scuPA and the bispecific antibody there was no degradation of fibrinogen after three hours of incubation, whereas in samples containing only scuPA there was a significant decrease in plasma fibrinogen. This absence of fibrinogen degradation demonstrates the fibrin specificity of the bispecific antibody. For example, when 1850 pM or 3700 pM of scuPA was added to the assay solution, clottable fibrinogen decreased from an initial level of approximately 266 mg/dL (measured in a sample without scuPA) to less than 87.3 mg/dL and 84.4 mg/dL, respectively, and precipitable fibrinogen decreased from an initial level of approximately 202 mg/dL (measured in a sample without scuPA) to 101 mg/dL 64.0 mg/dL, respectively. FIG. 19 shows the fibrinogenolysis observed over the entire range of scuPA concentrations tested in this assay.

DISCUSSION

A bispecific antibody was formed by chemically coupling antifibrin monoclonal antibody 59D8 to antiurokinase monoclonal antibody PEG2. When tested for the ability to lyse fibrin monomer and human plasma clots, the bispecific antibody increased both the fibrinolytic efficacy and fibrin specificity of scuPA. By chemically coupling radiolabeled forms of the two antibodies, it was possible to demonstrate that, as purified, the bispecific antibody consisted of a heterogeneous mixture of reaction products containing the two constituent antibodies in various ratios. Although it was not necessary to further purify the bispecific antibody mixture to demonstrate that it bound both antigens simultaneously and enhanced the fibrinolytic potency of scuPA, it may be possible to optimize the ratio of 59D8:PEG2 for fibrinolysis.

Runge et al. (Runge, M. S., et al., *Biochemistry* 27:1153–1157 (1988)) and Bode et al. (Bode, C., et al., *Science* 229:765–767 (1985); Bode, C., et al., *J. Mol. Cell. Cardiol.* 19:335–341 (1987)) have demonstrated that covalent (disulfide) conjugates of 59D8 and either urokinase or tPA are, respectively, 100 times more efficient than low molecular weight two-chain urokinase (Abbokinase, Abbott Laboratories) and 10 times more efficient than tPA in vitro. In the plasma clot system, the plasminogen activator-antifibrin antibody conjugates are 4-fold to 6-fold more potent than the parent plasminogen activators. These authors further demonstrated that the conjugates enhance clot lysis in an in vivo rabbit model (Runge, M. S., et al., *Proc. Natl. Acad. Sci. USA* 84:7659–7662 (1987)).

The approach described here further explores the concept of chemical conjugation. We demonstrate that fibrin binding can be imparted to a fibrinselective plasminogen activator (scuPA) that does not directly bind to fibrin.

It is understood that these descriptions, examples and embodiments are for illustrative purposes only, and that various modifications would be suggested within the spirit and purview of this application and the scope of the appended claims.

What is claimed is:

1. A heterobifunctional antibody having dual specificity wherein one of the dual specificities is specific for fibrin and the other specificity is specific for a thrombolytic agent, selected from the group consisting of tissue-type plasminogen activator (TPA), streptokinase, and urokinase.

2. The heterobifunctional antibody of claim 1 wherein a thrombolytic agent is bound to said heterobifunctional antibody.

3. The heterobinfunctional antibody of claim 1 comprising a Fab fragment of a monoclonal antibody specific for fibrin linked to a Fab fragment of a monoclonal antibody specific for a thrombolytic agent wherein said antibody is capable of binding fibrin and a thrombolytic agent simultaneously.

4. A method of lysing a thrombus comprising administering to a patient in need thereof, an effective amount of a heterobifunctional antibody having dual specificity wherein one of the dual specificities is specific for fibrin and the other specificity is specific for a thrombolytic agent selected from the group consisting of tissue-type plasminogen activator (TPA), streptokinase, and urokinase.

5. The method of claim 4 wherein said thrombolytic agent is a tissue-type plasminogen activator.

* * * * *